United States Patent
O'Connell

(10) Patent No.: US 9,861,310 B2
(45) Date of Patent: Jan. 9, 2018

(54) ALGORITHMS FOR DIABETES EXERCISE THERAPY

(71) Applicant: Exerscrip, LLC, New Haven, CT (US)

(72) Inventor: Charles O'Connell, New Haven, CT (US)

(73) Assignee: FITSCRIPT LLC, New Haven, CT (US)

( * ) Notice: Subject to any disclaimer, the term of this patent is extended or adjusted under 35 U.S.C. 154(b) by 63 days.

(21) Appl. No.: 14/885,825

(22) Filed: Oct. 16, 2015

(65) Prior Publication Data

US 2016/0106363 A1    Apr. 21, 2016

Related U.S. Application Data

(60) Provisional application No. 62/065,397, filed on Oct. 7, 2014, provisional application No. 62/194,357, filed (Continued)

(51) Int. Cl.
*A61B 5/00*    (2006.01)
*A61B 5/0205*    (2006.01)
(Continued)

(52) U.S. Cl.
CPC .......... *A61B 5/4839* (2013.01); *A61B 5/0004* (2013.01); *A61B 5/0205* (2013.01);
(Continued)

(58) Field of Classification Search
CPC . A61B 5/4839; A61B 5/14532; A61B 5/0004; A61B 5/0205; A61B 5/6801;
(Continued)

(56) References Cited

U.S. PATENT DOCUMENTS

| | | | |
|---|---|---|---|
| 5,474,552 A | * | 12/1995 | Palti .................... A61M 5/1723 604/67 |
| 5,591,104 A | | 1/1997 | Andrus et al. |

(Continued)

FOREIGN PATENT DOCUMENTS

| WO | WO-2004084976 A1 | 10/2004 |
|---|---|---|
| WO | WO-2006105146 A2 | 10/2006 |

OTHER PUBLICATIONS

Berg, E. The Artifical Pancreas Aces New Tests. "Bionic" volunteers venture into the real world of ice cream and red wine. Diabetes Forecast: The Healthy Living Magazine, Mar. 2014. Accessed online Nov. 3, 2015. http://www.diabetesforecast.org/2014/mar/the-artificial-pancreas-aces.html.

(Continued)

*Primary Examiner* — Manuel Mendez
(74) *Attorney, Agent, or Firm* — Wilson Sonsini Goodrich & Rosati

(57) ABSTRACT

Safe and effective exercise poses a specific set of challenges for subjects diagnosed with diabetes. These challenges include the coordination of exercise with blood glucose monitoring and insulin administration. Failure to coordinate these factors effectively can lead to various pathologies related to aberrant blood glucose levels. Presented herein are methods, systems, algorithms, computer program products, and computer-executable code for exercise guidance and instruction specific to diabetes relief and management. The approaches as disclosed herein can help ameliorate, slow, or reduce a likelihood of developing a diabetic condition.

20 Claims, 7 Drawing Sheets

Related U.S. Application Data on Jul. 20, 2015, provisional application No. 62/236,635, filed on Oct. 2, 2015.

(51) Int. Cl.
| | | |
|---|---|---|
| *A61M 5/172* | (2006.01) | |
| *A61B 5/145* | (2006.01) | |
| *G06F 19/00* | (2011.01) | |
| *A61M 5/14* | (2006.01) | |

(52) U.S. Cl.
CPC ........ *A61B 5/14532* (2013.01); *A61B 5/6801* (2013.01); *A61M 5/1723* (2013.01); *G06F 19/3468* (2013.01); *A61B 5/0022* (2013.01); *A61B 5/7275* (2013.01); *A61B 5/742* (2013.01); *A61M 5/14* (2013.01)

(58) Field of Classification Search
CPC ..... A61B 5/742; A61B 5/0022; A61B 5/7275; G06F 19/3468; A61M 5/1723; A61M 5/14
USPC ..... 604/65–67, 131, 151; 600/365, 345, 347
See application file for complete search history.

(56) References Cited

U.S. PATENT DOCUMENTS

| | | | |
|---|---|---|---|
| 7,949,382 B2 | 5/2011 | Jina | |
| 8,585,593 B2* | 11/2013 | Kovatchev | A61B 5/024 600/345 |
| 2006/0219576 A1 | 10/2006 | Jina | |
| 2007/0093750 A1 | 4/2007 | Jan et al. | |
| 2008/0139907 A1 | 6/2008 | Rao et al. | |
| 2008/0262469 A1* | 10/2008 | Brister | A61B 5/0002 604/504 |
| 2010/0286601 A1 | 11/2010 | Yodfat et al. | |
| 2010/0331652 A1* | 12/2010 | Groll | A61B 5/14532 600/365 |
| 2011/0184342 A1* | 7/2011 | Pesach | A61M 5/14248 604/65 |
| 2012/0226259 A1 | 9/2012 | Yodfat et al. | |
| 2012/0302990 A1 | 11/2012 | De Paula | |
| 2013/0165901 A1* | 6/2013 | Ruchti | A61M 5/1723 604/504 |
| 2014/0052722 A1 | 2/2014 | Bertsimas et al. | |

OTHER PUBLICATIONS

Castle, et al. Novel Use of Glucagon in a Closed-Loop System for Prevention of Hypoglycemia in Type 1 Diabetes. Diabetes Care, Jun. 2010, vol. 33, No. 6, pp. 1282-1287.

Charlie O'Connell Youtube Video with Transcript. Accessed online Nov. 3, 2015. https://www.youtube.com/watch?v=z70-5j_IgFA.

D-Fight! Total Body Exercise for Diabetes DVD Set with Transcript. Accessed Nov. 3, 2015.

dLifeTV Episode—Excercising with a Disability Youtube Video with Transcript. Accessed online Nov. 3, 2015. https://www.youtube.com/watch?v=18PffGRgMvg.

Fitscript Website: Fitness Prescriptions for Diabetes Prevention and Management. Accessed online Nov. 3, 2015. http://www.fitscript.com/.

Glucosezone: Youtube. Accessed online Nov. 3, 2015. https://www.youtube.com/user/GLUCOSEZONE.

International search report and written opinion dated Jan. 8, 2016 for PCT Application No. US2015/056089.

Jacobs, et al. Incorporating an Exercise Detection, Grading, and Hormone Dosing Algorithm Into the Artificial Pancreas Using Accelerometry and Heart Rate. J Diabetes Sci Technol Oct. 5, 2015.

Modules and Elements: Controller, CoreMD and Pancreum Wedges. Pancreum: The Wearable Artificial Pancreas Company Website. Accessed online Nov. 3, 2015. http://pancreum.com/modules-bionic-artificial-pancreas.html.

National Exercise Guidelines for Adults. dLife Website. Accessed online Nov. 3, 2015. http://www.dlife.com/diabetes-food-and-fitness/diabetes_and_exercise/exercise_guidelines?utm_source=dLife&utm_medium=dLifeTV&utm_content=TVThrow&utm_campaign=exerciseguide.

Scheiner, G. Getting Down to Basals. Diabetes Self-Management Website. Published Jul. 24, 2006. Accessed online Nov. 3, 2015. http://www.diabetesselfmanagement.com/managing-diabetes/treatment-approaches/getting-down-to-basals/.

Weinstock, R. Closing the Loop: Another Step Forward. Diabetes Care, Sep. 2011, vol. 34, No. 9, pp. 2136-2137.

* cited by examiner

ALGORITHMS FOR DIABETES EXERCISE THERAPY

CROSS-REFERENCE TO RELATED APPLICATIONS

This application claims the benefit of priority to U.S. Provisional Patent Application Ser. No. 62/065,397, filed on Oct. 17, 2014; U.S. Provisional Patent Application Ser. No. 62/194,357, filed on Jul. 20, 2015; and U.S. Provisional Patent Application Ser. No. 62/236,635, filed on Oct. 2, 2015, the contents of each of which is hereby incorporated by reference in its entirety.

BACKGROUND

Safe and effective exercise poses a specific set of challenges for subjects diagnosed with diabetes. These challenges include the coordination of exercise with glucose monitoring and administration of medications. Failure to coordinate these factors effectively can lead to various pathologies, including headache, seizure, faintness, withdrawal, depression, and hypoglycemia.

SUMMARY OF THE INVENTION

In some embodiments, the disclosure provides a method comprising: a) administering to a subject a basal dose of insulin, wherein the subject is in need thereof, and wherein the subject is diabetic; b) subsequent to the administering to the subject the basal dose of insulin, administering to the subject an adjusted dose of insulin, wherein the adjusted dose of insulin is from about 5% to about 95% of the basal dose of insulin; c) subsequent to the administering to the subject the adjusted dose of insulin, sustaining the subject's heart rate at a level that is from 10%-50% of the subject's maximum heart rate for at least 30 minutes; and d) subsequent to the sustaining the subject's heart rate at the level that is from 10%-50% of the subject's maximum heart rate for at least 30 minutes, elevating the subject's heart rate to a level that is at least 50% of the subject's maximum heart rate.

In some embodiments, the disclosure provides a method comprising: a) administering to a subject a basal dose of insulin, wherein the subject is in need thereof, and wherein the subject is diabetic; b) receiving from the subject a selection of an exercise that the subject is to perform; c) determining based on the exercise that the subject is to perform an adjusted dose of insulin for administration to the subject, wherein the adjusted dose of insulin is from about 5% to about 95% of the basal dose of insulin; d) administering to the subject the adjusted dose of insulin; e) subsequent to the administering to the subject the adjusted dose of insulin, sustaining the subject's heart rate at a level that is from 10%-50% of the subject's maximum heart rate for at least 30 minutes; and f) subsequent to the sustaining the subject's heart rate at the level that is from 10%-50% of the subject's maximum heart rate for at least 30 minutes, monitoring the subject's heart rate to detect an elevation in the subject's heart rate, wherein the elevation in the subject's heart rate is to a level that is at least 50% of the subject's maximum heart rate.

In some embodiments, the disclosure provides a method comprising: a) receiving by a subject a basal dose of insulin, wherein the subject is in need thereof, and wherein the subject is diabetic; b) subsequent to the receiving the basal dose of insulin, receiving by the subject an adjusted dose of insulin, wherein the adjusted dose of insulin is from about 5% to about 95% of the basal dose of insulin; c) subsequent to the receiving by the subject the adjusted dose of insulin, sustaining by the subject the subject's heart rate at a level that is from 10%-50% of the subject's maximum heart rate for at least 30 minutes; and d) subsequent to the sustaining the subject's heart rate at the level that is from 10%-50% of the subject's maximum heart rate for at least 30 minutes, elevating by the subject the subject's heart rate to a level that is at least 50% of the subject's maximum heart rate.

In some embodiments, the disclosure provides a system comprising: a) a telecommunications device; b) an insulin delivery device that is: 1) in contact with a subject; 2) in communication with the telecommunications device; 3) configured to administer insulin to the subject; and 4) configured to receive from the telecommunications device a transmission of an instruction to administer to the subject a dose of insulin; and c) a glucose monitoring device that is: 1) in contact with the subject; 2) in communication with the telecommunications device; 3) configured to detect a glucose level in the subject; and 4) configured to transmit to the telecommunications device a reading of the glucose level in the subject, wherein the telecommunications device sends a transmission from the telecommunications device to the insulin delivery device, wherein the transmission instructs the insulin delivery device to administer to the subject an adjusted dose of insulin over a period of at least 30 minutes, wherein the adjusted dose of insulin is from about 5% to about 95% of a basal dose of insulin for the subject.

In some embodiments, the disclosure provides a system comprising: a) a telecommunications device; b) an insulin delivery device that is: 1) in contact with a subject; 2) in communication with the telecommunications device; 3) configured to administer insulin to the subject; and 4) configured to receive from the telecommunications device a transmission of an instruction to administer to the subject a dose of insulin; c) a glucose monitoring device that is: 1) in contact with the subject; 2) in communication with the telecommunications device; 3) configured to detect a glucose level in the subject; and 4) configured to transmit to the telecommunications device a reading of the glucose level in the subject; and d) a heart rate monitor device that is: 1) in contact with the subject; 2) in communication with the telecommunications device; 3) configured to detect a heart rate in the subject; and 4) configured to transmit to the telecommunications device a reading of the heart rate in the subject, wherein the telecommunications device sends a transmission from the telecommunications device to the insulin delivery device, wherein the transmission instructs the insulin delivery device, based on the reading of the heart rate of the subject, to administer to the subject an adjusted dose of insulin over a period of at least 30 minutes, wherein the adjusted dose of insulin is from about 5% to about 95% of a basal dose of insulin for the subject.

In some embodiments, the disclosure provides a system comprising: a) an insulin delivery device that is: 1) in contact with a subject; 2) configured to administer insulin to the subject; and 3) configured to receive a transmission of an instruction to administer to the subject a dose of insulin; and b) a glucose monitoring device that is: 1) in contact with the subject; 2) in communication with the insulin delivery device; 3) configured to detect a glucose level in the subject; and 4) configured to transmit to the insulin delivery device an instruction to administer to the subject the dose of insulin based on the detected glucose level in the subject, wherein the insulin delivery device comprises a processor and a computer-readable medium with a computer-executable code encoded thereon, wherein the computer-executable code instructs the insulin delivery device to administer to the subject an adjusted dose of insulin over a period of at least 30 minutes, wherein the adjusted dose of insulin is from about 5% to about 95% of a basal dose of insulin for the subject, and wherein the processor processes the computer-executable code.

In some embodiments, the disclosure provides a system comprising: a) an insulin delivery device that is: 1) in contact with a subject; 2) configured to administer insulin to the subject; and 3) configured to receive a transmission of an instruction to administer to the subject a dose of insulin; and b) a glucose monitoring device that is: 1) in contact with the subject; 2) in communication with the insulin delivery device; 3) configured to detect a glucose level in the subject; and 4) configured to transmit to the insulin delivery device an instruction to administer to the subject the dose of insulin based on the detected glucose level in the subject, wherein the glucose monitoring device sends a transmission from the glucose monitoring device to the insulin delivery device, wherein the transmission instructs the insulin delivery device to administer to the subject an adjusted dose of insulin over a period of at least 30 minutes, wherein the adjusted dose of insulin is from about 5% to about 95% of a basal dose of insulin for the subject.

In some embodiments, the disclosure provides a kit comprising: a) an insulin delivery device; and b) a glucose monitoring device, wherein the insulin delivery device comprises a processor and a computer-readable medium with a computer-executable code encoded thereon, wherein the computer-executable code instructs the insulin delivery device to administer to a subject an adjusted dose of insulin over a period of at least 30 minutes, wherein the adjusted dose of insulin is from about 5% to about 95% of a basal dose of insulin for the subject, and wherein the processor processes the computer-executable code.

In some embodiments, the disclosure provides a kit comprising: a) a telecommunications device; b) an insulin delivery device; and c) a glucose monitoring device, wherein the telecommunications device comprises a processor and a computer-readable medium with a computer-executable code encoded thereon, wherein the computer-executable code instructs the telecommunications device to transmit to the insulin delivery device an instruction to administer to a subject an adjusted dose of insulin over a period of at least 30 minutes, wherein the adjusted dose of insulin is from about 5% to about 95% of a basal dose of insulin for the subject, and wherein the processor processes the computer-executable code.

In some embodiments, the disclosure provides a kit comprising: a) an insulin delivery device; and b) a glucose monitoring device, wherein the glucose monitoring device comprises a processor and a computer-readable medium with a computer-executable code encoded thereon, wherein the computer-executable code instructs the glucose monitoring device to transmit to the insulin delivery device an instruction to administer to a subject an adjusted dose of insulin over a period of at least 30 minutes, wherein the adjusted dose of insulin is from about 5% to about 95% of a basal dose of insulin for the subject, and wherein the processor processes the computer-executable code.

In some embodiments, the disclosure provides a method comprising: a) presenting by a media device to a subject an electronic communication medium that provides instruction for physical exercise, wherein the subject is diabetic, wherein the media device is in communication with a receiver; b) monitoring, contemporaneously with presenting to the subject the electronic communication medium that provides instruction for physical exercise, via a glucose monitoring device the subject during a state of physical exercise, wherein the glucose monitoring device detects a blood glucose level in the subject; c) transmitting by a biometric device the blood glucose level of the subject to the receiver; d) receiving by the receiver the blood glucose level of the subject; and e) presenting by the media device an indication of a change in the blood glucose level of the subject in real time contemporaneously with presenting the electronic communication medium that provides instruction for physical exercise.

DETAILED DESCRIPTION OF THE INVENTION

Figure 1:
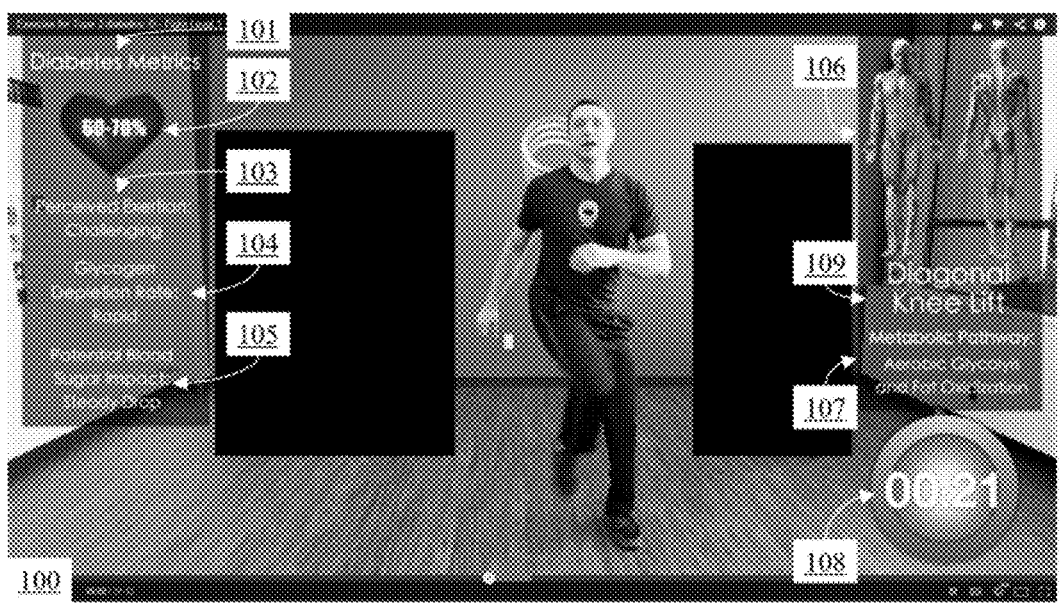
FIG. 1 illustrates an audiovisual data stream.

The invention provides methods, systems, algorithms, computer programs, kits, devices, and computer-executable code for exercise guidance and instruction specific to diabetes relief and management, and the slowing or reducing a likelihood of developing a diabetic condition. The methods, systems, algorithms, computer programs, kits, devices, and computer-executable code are based in part on correlations and interrelationships among variables associated with glucose and insulin levels during exercise.

Diabetes

In some embodiments, a subject using a method, system, algorithm, computer program, kit, device, or computer-executable code of the disclosure is diagnosed with diabetes. Non-limiting examples of diabetes include diabetes mellitus, type 1 diabetes, type 2 diabetes, prediabetes, gestational diabetes, latent autoimmune diabetes of adults, congenital diabetes, cystic fibrosis-related diabetes, steroid diabetes, and monogenic diabetes.

Diabetes is a group of metabolic diseases in which high blood sugar levels persist over a prolonged period. Symptoms of high blood sugar include frequent urination, increased thirst, and increased hunger. If left untreated, diabetes can cause many complications. Acute complications include diabetic ketoacidosis and nonketotic hyperosmolar coma. Chronic complications include cardiovascular disease, stroke, chronic kidney failure, foot ulcers, and damage to the eyes.

Diabetes is caused by either failure of the pancreas to produce sufficient insulin, or the cells of the body not responding properly to the insulin produced. Type 1 diabetes results from the pancreas's inability to produce enough insulin. Type 2 diabetes begins with insulin resistance, a condition in which cells and tissues fail to respond to insulin properly. As the disease progresses, a lack of insulin can also develop. A primary cause is excessive body weight and insufficient exercise. Gestational diabetes is the third main form, and occurs when pregnant women without a previous history of diabetes develop a high blood sugar level.

Non-limiting examples of symptoms of diabetes include weight loss, increased urination or polyuria, increased thirst or polydipsia, increased hunger or polyphagia, blurry vision, headache, fatigue, slow healing of cuts, itchy skin, changes in the shape of the lens of the eye, and skin rashes or dermadromes. Low blood sugar or hypoglycemia is prevalent in subjects with type 1 and type 2 diabetes. Non-limiting examples of hypoglycemic symptoms include feelings of unease, sweating, trembling, increased appetite, confusion, changes in behavior, seizures, unconsciousness, and permanent brain damage. Subjects, such as those diagnosed with type 1 diabetes, can also experience episodes of diabetic ketoacidosis, a metabolic disturbance characterized by nausea, vomiting and abdominal pain, the scent of acetone on the breath, deep breathing known as Kussmaul breathing, and in severe cases, reduced consciousness. Subjects, such as those diagnosed with type 2 diabetes, can also experience a hyperosmolar nonketotic state, which is the result of dehydration.

Non-limiting examples of long-term complications due to diabetes include damage to blood vessels, cardiovascular disease, coronary artery disease, stroke, peripheral vascular disease, and damage to blood vessels of the eyes, kidneys, and nerves. Damage to blood vessels of the eyes, also known as diabetic retinopathy, can result in gradual vision loss and blindness. Damage to blood vessels of the kidneys, known as diabetic nephropathy, can result in tissue scarring, urine protein loss, and eventually chronic kidney disease. Damage to blood vessels of the nerves, known as diabetic neuropathy, can result in numbness, tingling, pain, altered pain sensation, leading to damage of the skin, and painful muscle wasting and weakness. Diabetes-related foot problems, such as diabetic foot ulcers, can occur and result in amputation.

Non-limiting examples of possible risks that can occur during exercise include hypoglycemia, hyperglycemia, insulin shock, diabetic shock, low heart rate, high heart rate, fainting, unconsciousness, and death.

Co-medications of Insulin and Co-morbidities with Diabetics

In some embodiments, the methods, systems, algorithms, computer programs, kits, devices, and computer-executable code include administration of an insulin. Non-limiting examples of insulins include regular insulin, insulin glulisine, insulin lispro, insulin aspart, insulin lispro protamine, insulin insulin aspart protamine, insulin neutral protamine Hagedorn (NPH), insulin glargine, and insulin detemir. In some embodiments, the insulin is a mixture of insulin. Non-limiting examples of mixtures of insulin include about 30% regular insulin and about 70% insulin NPH; about 50% insulin lispro and about 50% insulin lispro protamine; about 25% insulin lispro and about 75% insulin lispro protamine; and about 30% insulin aspart and about 70% insulin aspart protamine.

In some embodiments, the methods, systems, algorithms, computer programs, kits, devices, and computer-executable code provided incorporate information relating to a medication taken by the subject that can alter how an exercise instruction of the disclosure modulates blood sugar. Non-limiting examples of medications include anti-diabetic medications, blood pressure medications, anti-inflammatory medications, acid reflux medications, and anti-arthritic medications. Non-limiting examples of anti-diabetic medications include metformin, phenformin, buformin, rosiglitazone, pioglitazone, troglitazone, canagliflozin, dapagliflozin, miglitol, acarbose, repaglinide, nateglinide, gliquidone, glimepiride, gliclazide, and glipizide.

In some embodiments, a subject of the disclosure engaging in exercise exhibits co-morbidities that, along with diabetes, can affect how exercise modulates blood glucose. Non-limiting examples of co-morbidities include heart disease, hypertension, kidney problems, liver problems, strokes, and joint issues.

Non-limiting examples of suitable variables include established safety guidelines for glucose levels before during and after exercise; time of day and duration of activity; heart rate level and perceived exertion level; muscle fiber recruitment and activity performed; presence of insulin and medication; and food consumed.

Each variable can have a unique and distinguishable impact on glucose levels during exercise. In some embodiments, based on different implementations of combinations of the variables, the disclosure can provide exercise recommendations and instruction targeting specific and desired diabetes metrics outcomes. Non-limiting examples of such outcomes include A1C reduction; increase in insulin sensitivity; decrease in insulin resistance; fat metabolism and weight loss; real-time reduction of blood glucose levels; and real-time elevation of blood glucose levels. In some embodiments, the disclosure can provide exercise recommendations and instruction targeting specific and desired cardiovascular and pulmonary outcomes. Non-limiting examples of such outcomes include increased muscle tone; increased cardiac stress resistance; and increased lung function.

Exercise Guidance Based Upon Target Heart Rates

In some embodiments, the methods of the disclosure are adaptable and are designed to achieve specific outcomes related to type 1 diabetes, such as reduced insulin dependence. In some embodiments, the methods of the disclosure are adaptable and are designed to achieve specific outcomes related to type 2 diabetes. Non-limiting examples of such outcomes include A1C reduction; increased fat metabolism; increased weight loss; real-time decrease of blood glucose levels; increase in insulin sensitivity; and decrease in insulin resistance.

In some embodiments, a collection of exercises is preselected to achieve the desired diabetes metrics listed above. Each suggested exercise is pre-selected to meet at least one of the following criteria: be performed in a heart rate zone from 50% to 100% of a maximum heart rate and correlating exertion level that does not cross the anaerobic threshold and does not stimulate the raising of glucose levels; utilizes either aerobic glycolysis or fat oxidization as the metabolic pathway for the provision of energy; causes the systematic depletion of glycogen stores within specific skeletal muscle without stimulating a glycolytic response from the liver, such as release of stored glycogen into the blood stream resulting in a rise in glucose levels, resulting in an increase in insulin sensitivity and decrease in insulin resistance; and be performed for an amount of time that stimulates the systematic depletion of glycogen stores within selected skeletal musculature.

Based on the subject's level of physical fitness, severity of diabetic symptoms, and exercise preferences, the subject can choose a target heart rate for an exercise session. The target heart rate can be determined as a percentage of the subject's maximum heart rate. The heart rate can also be chosen based on the level of physical exertion that the subject chooses to experience. Once the subject has chosen a target heart rate, the subject can plan for the glucose and insulin levels that are suitable for the target heart zone. The subject can thus establish target ranges or target values for various biometric parameters, such as heart rate, glucose level, and insulin level. The subject can also establish rates of administration for insulin and glucagon.

For example, a subject can find that exercise that promotes a heart rate of from 50% to 60% of the subject's maximum heart rate is easy and comfortable. This heart rate can cause a small decrease in glucose levels, as most of the subject's energy consumed is carbohydrate. The subject should maintain a level of insulin that is appropriate for the subject's carbohydrate consumption.

A subject can find that exercise that promotes a heart rate of from 60% to 70% of the subject's maximum heart rate is challenging and beneficial. This heart rate functions as a fat-burning zone. Significant decreases in glucose levels are possible. The subject should maintain a level of insulin that is appropriate for the subject's carbohydrate consumption.

A subject can find that exercise that promotes a heart rate of from 70% to 80% of the subject's maximum heart rate is hard. In this zone, the subject's energy consumption is approximately half carbohydrate and half fat. A subject can experience a risk of hypoglycemia, and a significant drop in blood glucose levels is possible. A subject can reduce insulin levels to aid in avoiding hypoglycemia.

A subject can find that exercise that promotes a heart rate of from 80% to 90% of the subject's maximum heart rate is very hard. The subject's energy expenditure is approximately 85% carbohydrate, 15% fat, and a small amount of protein. The subject's glucose levels can fluctuate, and the ability to store and produce glycogen can vary significantly based on physical fitness.

A subject can find that exercise that promotes a heart rate of from 90% to 100% of the subject's maximum heart rate is the subject's maximum possible effort. The subject's energy expenditure is approximately 90% carbohydrate, 10% fat, and a small amount of protein. The subject's glucose levels can rise, possibly to an unsafe level, especially if the subject simultaneously consumes a food containing a significant carbohydrate portion.

The maximum heart rate of the subject can be estimated in several ways. In some embodiments, the maximum heart rate is estimated by the following:

Maximum heart rate (in beats per minute [bpm])
=220−(age of the subject [age]);

In some embodiments, the maximum heart rate is estimated by the following:

Maximum heart rate (in bpm)=208−(0.7×age);

In some embodiments, the maximum heart rate is estimated by the following:

Maximum heart rate (in bpm)=207−(0.7×age);

In some embodiments, the maximum heart rate is estimated by a treadmill test. The treadmill test entails a subject running on a treadmill while connected to heart rate monitors and blood pressure monitors. At various periods of time, the treadmill accelerates and the incline rises, until the subject reaches the maximum sustained effort. The measured heart rate of the subject at the maximum sustained effort is the maximum heart rate of the subject.

Rather than choosing a target heart rate, a subject can also choose a desired exercise to perform, and input the desired exercise into any system herein. Based on the subject's choice of exercise, and other factors, a system of the invention can approve, disapprove, or modify the desired exercise. A system herein can also modulate the subject's insulin administration rate or glucagon administration rate based on choice of exercise; heart rate, for example, real time heart rate as detected during exercise; glucose level, for example, real time blood glucose level as detected during exercise; or electronically-stored records of the subject's past exercise performance and diabetes risk factors, such as nutrition, time of day, and general level of physical fitness.

In some embodiments, prior to the subject being in a state of physical exercise, while the subject is in a state of physical rest, a heart rate of the subject at a resting level is from about 10% to about 50% of the maximum heart rate of the subject. In some embodiments, the heart rate of the subject at the resting level is from about 10% to about 15%, from about 15% to about 20%, from about 20% to about 25%, from about 25% to about 30%, from about 30% to about 35%, from about 35% to about 40%, from about 40% to about 45%, or from about 45% to about 50% of the maximum heart rate of the subject.

In some embodiments, subsequent to the subject being in the state of physical rest, while the subject is in the state of physical exercise, the heart rate of the subject is elevated to an active level that is from about 50% to about 100% of the maximum heart rate of the subject. In some embodiments, the heart rate of the subject is elevated to the active level that is from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or from about 95% to about 100% of the maximum heart rate of the subject.

A subject can also approximate heart rate based on comparison to a physical activity. A subject can plan to exercise at a heart rate level that is comparable to the heat rate experience, for example, during walking, jogging, running, swimming, cycling, golfing, or playing a sport.

In some embodiments, the subject receives or is administered a dose of a hormone at a basal rate. Non-limiting examples of hormones to be administered include insulin, glucagon, adrenaline, and corticosteroids, such as cortisol. In some embodiments, the basal rate of the dose of hormone is from about 2 units per day (U/d) to about 50 U/d. In some embodiments, the basal rate of the dose of hormone is from about 2 U/d to about 20 U/d, from about 5 U/d to about 50 U/d, from about 5 U/d to about 40 U/d, or from about 10 U/d to about 50 U/d. In some embodiments, the basal rate of the dose of hormone is from about 2 U/d to about 3 U/d, from about 3 U/d to about 4 U/d, from about 4 U/d to about 5 U/d, from about 5 U/d to about 6 U/d, from about 6 U/d to about 7 U/d, from about 7 U/d to about 8 U/d, from about 8 U/d to about 9 U/d, from about 9 U/d to about 10 U/d, from about 10 U/d to about 11 U/d, from about 11 U/d to about 12 U/d, from about 12 U/d to about 13 U/d, from about 13 U/d to about 14 U/d, from about 14 U/d to about 15 U/d, from about 15 U/d to about 16 U/d, from about 16 U/d to about 17 U/d, from about 17 U/d to about 18 U/d, from about 18 U/d to about 19 U/d, from about 19 U/d to about 20 U/d, from about 20 U/d to about 21 U/d, from about 21 U/d to about 22 U/d, from about 22 U/d to about 23 U/d, from about 23 U/d to about 24 U/d, from about 24 U/d to about 25 U/d, from about 25 U/d to about 26 U/d, from about 26 U/d to about 27 U/d, from about 27 U/d to about 28 U/d, from about 28 U/d to about 29 U/d, from about 29 U/d to about 30 U/d, from about 30 U/d to about 31 U/d, from about 31 U/d to about 32 U/d, from about 32 U/d to about 33 U/d, from about 33 U/d to about 34 U/d, from about 34 U/d to about 35 U/d, from about 35 U/d to about 36 U/d, from about 36 U/d to about 37 U/d, from about 37 U/d to about 38 U/d, from about 38 U/d to about 39 U/d, from about 39 U/d to about 40 U/d, from about 40 U/d to about 41 U/d, from about 41 U/d to about 42 U/d, from about 42 U/d to about 43 U/d, from about 43 U/d to about 44 U/d, from about 44 U/d to about 45 U/d, from about 45 U/d to about 46 U/d, from about 46 U/d to about 47 U/d, from about 47 U/d to about 48 U/d, from about 48 U/d to about 49 U/d, or from about 49 U/d to about 50 U/d.

In some embodiments, the basal rate of the dose of hormone is from about 0.05 units per hour (U/h) to about 2.2 U/h. In some embodiments, the basal rate of the dose of hormone is from about 0.05 U/h to about 0.9 U/h, from about 0.2 U/h to about 2.2 U/h, from about 0.2 U/h to about 1.8 U/h, or from about 0.3 U/h to about 2.2 U/h. In some embodiments, the basal rate of the dose of hormone is from about 0.05 U/h to about 0.1 U/h, from about 0.1 U/h to about 0.15 U/h, from about 0.15 U/h to about 0.2 U/h, from about 0.2 U/h to about 0.25 U/h, from about 0.25 U/h to about 0.3 U/h, from about 0.3 U/h to about 0.35 U/h, from about 0.35 U/h to about 0.4 U/h, from about 0.4 U/h to about 0.45 U/h, from about 0.45 U/h to about 0.5 U/h, from about 0.5 U/h to about 0.55 U/h, from about 0.55 U/h to about 0.6 U/h, from about 0.6 U/h to about 0.65 U/h, from about 0.65 U/h to about 0.7 U/h, from about 0.7 U/h to about 0.75 U/h, from about 0.75 U/h to about 0.8 U/h, from about 0.8 U/h to about 0.85 U/h, from about 0.85 U/h to about 0.9 U/h, from about 0.9 U/h to about 0.95 U/h, from about 0.95 U/h to about 1 U/h, from about 1 U/h to about 1.05 U/h, from about 1.05 U/h to about 1.1 U/h, from about 1.1 U/h to about 1.15 U/h, from about 1.15 U/h to about 1.2 U/h, from about 1.2 U/h to about 1.25 U/h, from about 1.25 U/h to about 1.3 U/h, from about 1.3 U/h to about 1.35 U/h, from about 1.35 U/h to about 1.4 U/h, from about 1.4 U/h to about 1.45 U/h, from about 1.45 U/h to about 1.5 U/h, from about 1.5 U/h to about 1.55 U/h, from about 1.55 U/h to about 1.6 U/h, from about 1.6 U/h to about 1.65 U/h, from about 1.65 U/h to about 1.7 U/h, from about 1.7 U/h to about 1.75 U/h, from about 1.75 U/h to about 1.8 U/h, from about 1.8 U/h to about 1.85 U/h, from about 1.85 U/h to about 1.9 U/h, from about 1.9 U/h to about 1.95 U/h, from about 1.95 U/h to about 2 U/h, from about 2 U/h to about 2.05 U/h, from about 2.05 U/h to about 2.1 U/h, from about 2.1 U/h to about 2.15 U/h, or from about 2.15 U/h to about 2.2 U/h.

In some embodiments, the subject receives or is administered the dose of hormone at an adjusted rate. The adjusted rate of the dose of hormone is determined relative to the basal rate of the dose of hormone. In some embodiments, the adjusted rate of the dose of hormone is about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.9%, about 101%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200%, about 250%, about 300%, about 350%, about 400%, about 450%, about 500%, about 550%, about 600%, about 650%, about 700%, about 750%, about 800%, about 850%, about 900%, about 950%, or about 1000% of the basal rate of the dose of hormone.

In some embodiments, the adjusted rate of the dose of hormone is from about 0.1% to about 0.5%, from about 0.5% to about 1%, from about 1% to about 5%, from about 5% to about 10 from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 91%, from about 91% to about 92%, from about 92% to about 93%, from about 93% to about 94%, from about 94% to about 95%, from about 95% to about 96%, from about 96% to about 97%, from about 97% to about 98%, from about 98% to about 99%, from about 99% to about 99.5%, from about 99.5% to about 99.9%, from about 101% to about 105%, from about 105% to about 110%, from about 110% to about 115%, from about 115% to about 120%, from about 120% to about 125%, from about 125% to about 130%, from about 130% to about 135%, from about 135% to about 140%, from about 140% to about 145%, from about 145% to about 150%, from about 150% to about 155%, from about 155% to about 160%, from about 160% to about 165%, from about 165% to about 170%, from about 170% to about 175%, from about 175% to about 180%, from about 180% to about 185%, from about 185% to about 190%, from about 190% to about 195%, from about 195% to about 200%, from about 200% to about 250%, from about 250% to about 300%, from about 300% to about 350%, from about 350% to about 400%, from about 400% to about 450%, from about 450% to about 500%, from about 500% to about 550%, from about 550% to about 600%, from about 600% to about 650%, from about 650% to about 700%, from about 700% to about 750%, from about 750% to about 800%, from about 800% to about 850%, from about 850% to about 900%, from about 900% to about 950%, or from about 950% to about 1000% of the basal rate of the dose of hormone.

In some embodiments, the adjusted rate of the dose of insulin is about 15% of the basal rate of the dose of insulin, and the heart rate of the subject is elevated to an active level that is from about 50% to about 60% of the maximum heart rate of the subject. In some embodiments, the adjusted rate of the dose of insulin is about 15% of the basal rate of the dose of insulin, and the heart rate of the subject is elevated to an active level that is from about 60% to about 70% of the maximum heart rate of the subject. In some embodiments, the adjusted rate of the dose of insulin is about 50% of the basal rate of the dose of insulin, and the heart rate of the subject is elevated to an active level that is from about 70% to about 80% of the maximum heart rate of the subject. In some embodiments, the adjusted rate of the dose of insulin is about 85% of the basal rate of the dose of insulin, and the heart rate of the subject is elevated to an active level that is from about 80% to about 90% of the maximum heart rate of the subject. In some embodiments, the adjusted rate of the dose of insulin is about 90% of the basal rate of the dose of insulin, and the heart rate of the subject is elevated to an active level that is from about 90% to about 100% of the maximum heart rate of the subject.

In some embodiments, the adjusted rate of the dose of hormone is received by or administered to the subject for a time period while the heart rate of the subject is at the resting level. In some embodiments, the time period is at least about 5 minutes, at least about 10 minutes, at least about 15 minutes, at least about 20 minutes, at least about 25 minutes, at least about 30 minutes, at least about 35 minutes, at least about 40 minutes, at least about 45 minutes, at least about 50 minutes, at least about 55 minutes, at least about one hour, at least about 90 minutes, at least about two hours, at least about 150 minutes, at least about three hours, at least about four hours, at least about five hours, or at least about six hours.

In some embodiments, the time period is from about 5 minutes to about 6 hours. In some embodiments, the time period is from about 5 minutes to about 90 minutes. In some embodiments, the time period is from about 5 minutes to about 10 minutes, from about 10 minutes to about 15 minutes, from about 15 minutes to about 20 minutes, from about 20 minutes to about 25 minutes, from about 25 minutes to about 30 minutes, from about 30 minutes to about 35 minutes, from about 35 minutes to about 40 minutes, from about 40 minutes to about 45 minutes, from about 45 minutes to about 50 minutes, from about 50 minutes to about 55 minutes, from about 55 minutes to about 60 minutes, from about 60 minutes to about 65 minutes, from about 65 minutes to about 70 minutes, from about 70 minutes to about 75 minutes, from about 75 minutes to about 80 minutes, from about 80 minutes to about 85 minutes, from about 85 minutes to about 90 minutes, from about 90 minutes to about 120 minutes, from about 120 minutes to about 150 minutes, from about 150 minutes to about 180 minutes, from about 180 minutes to about 240 minutes, from about 240 minutes to about 300 minutes, or from about 300 minutes to about 360 minutes.

In some embodiments, the methods of the disclosure include measuring the glucose level of the subject during the state of physical exercise. In some embodiments, the glucose level measured during the state of physical exercise is outside of a critical glucose range. In some embodiments, the critical glucose range is from about 70 mg/dL to about 250 mg/dL. In some embodiments, the critical glucose range is from about 100 mg/dL to about 250 mg/dL. In some embodiments, the critical glucose range is from about 70 mg/dL to about 140 mg/dL. In some embodiments, the critical glucose range is from about 100 mg/dL to about 140 mg/dL. In some embodiments, the critical glucose range is from about 70 mg/dL to about 75 mg/dL, from about 75 mg/dL to about 80 mg/dL, from about 80 mg/dL to about 85 mg/dL, from about 85 mg/dL to about 90 mg/dL, from about 90 mg/dL to about 95 mg/dL, from about 95 mg/dL to about 100 mg/dL, from about 100 mg/dL to about 105 mg/dL, from about 105 mg/dL to about 110 mg/dL, from about 110 mg/dL to about 115 mg/dL, from about 115 mg/dL to about 120 mg/dL, from about 120 mg/dL to about 125 mg/dL, from about 125 mg/dL to about 130 mg/dL, from about 130 mg/dL to about 135 mg/dL, from about 135 mg/dL to about 140 mg/dL, from about 140 mg/dL to about 145 mg/dL, from about 145 mg/dL to about 150 mg/dL, from about 150 mg/dL to about 155 mg/dL, from about 155 mg/dL to about 160 mg/dL, from about 160 mg/dL to about 165 mg/dL, from about 165 mg/dL to about 170 mg/dL, from about 170 mg/dL to about 175 mg/dL, from about 175 mg/dL to about 180 mg/dL, from about 180 mg/dL to about 185 mg/dL, from about 185 mg/dL to about 190 mg/dL, from about 190 mg/dL to about 195 mg/dL, from about 195 mg/dL to about 200 mg/dL, from about 200 mg/dL to about 205 mg/dL, from about 205 mg/dL to about 210 mg/dL, from about 210 mg/dL to about 215 mg/dL, from about 215 mg/dL to about 220 mg/dL, from about 220 mg/dL to about 225 mg/dL, from about 225 mg/dL to about 230 mg/dL, from about 230 mg/dL to about 235 mg/dL, from about 235 mg/dL to about 240 mg/dL, from about 240 mg/dL to about 245 mg/dL, or from about 245 mg/dL to about 250 mg/dL.

In some embodiments, based upon a measurement of the glucose level of the subject outside of the critical glucose range, an action is performed to restore the glucose level to within the critical glucose range. In some embodiments, the glucose level is below the critical glucose range, and the action is the consumption of a carbohydrate by the subject. Non-limiting examples of carbohydrates include slow-acting carbohydrates, fast-acting carbohydrates, chewable carbohydrates, dissolvable carbohydrates, glucose carbohydrates, sucrose carbohydrates, and fructose carbohydrates. In some embodiments, the glucose level is outside the critical glucose range, and the action is the adjustment of the dose of hormone to a second adjusted rate. In some embodiments, the glucose level is outside of the critical glucose range, and the action is a second state of physical exercise.

In some embodiments, the second adjusted rate of the dose of hormone is determined relative to the adjusted rate of the dose of hormone. In some embodiments, the second adjusted rate of the dose of hormone is about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.9%, about 101%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200%, about 250%, about 300%, about 350%, about 400%, about 450%, about 500%, about 550%, about 600%, about 650%, about 700%, about 750%, about 800%, about 850%, about 900%, about 950%, or about 1000% of the adjusted rate of the dose of hormone.

In some embodiments, the second adjusted rate of the dose of hormone is from about 0.1% to about 0.5%, from about 0.5% to about 1%, from about 1% to about 5%, from about 5% to about 10 from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 91%, from about 91% to about 92%, from about 92% to about 93%, from about 93% to about 94%, from about 94% to about 95%, from about 95% to about 96%, from about 96% to about 97%, from about 97% to about 98%, from about 98% to about 99%, from about 99% to about 99.5%, from about 99.5% to about 99.9%, from about 101% to about 105%, from about 105% to about 110%, from about 110% to about 115%, from about 115% to about 120%, from about 120% to about 125%, from about 125% to about 130%, from about 130% to about 135%, from about 135% to about 140%, from about 140% to about 145%, from about 145% to about 150%, from about 150% to about 155%, from about 155% to about 160%, from about 160% to about 165%, from about 165% to about 170%, from about 170% to about 175%, from about 175% to about 180%, from about 180% to about 185%, from about 185% to about 190%, from about 190% to about 195%, from about 195% to about 200%, from about 200% to about 250%, from about 250% to about 300%, from about 300% to about 350%, from about 350% to about 400%, from about 400% to about 450%, from about 450% to about 500%, from about 500% to about 550%, from about 550% to about 600%, from about 600% to about 650%, from about 650% to about 700%, from about 700% to about 750%, from about 750% to about 800%, from about 800% to about 850%, from about 850% to about 900%, from about 900% to about 950%, or from about 950% to about 1000% of the adjusted rate of the dose of hormone.

In some embodiments, subsequent to the subject being in the state of physical exercise, while the subject is in the second state of physical exercise, the heart rate of the subject is modified to a second active level that is from about 50% to about 100% of the maximum heart rate of the subject. In some embodiments, the heart rate of the subject is elevated to the active level that is from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or from about 95% to about 100% of the maximum heart rate of the subject.

In some embodiments, the glucose level of the subject during the state of physical exercise is above the critical glucose range and the heart rate of the subject is modified to the second active level that is from about 50% to about 60%, from about 60% to about 70%, or from about 70% to about 80% of the maximum heart rate of the subject. In some embodiments, the glucose level of the subject during the state of physical exercise is below the critical glucose range and the heart rate of the subject is modified to the second active level that is from about 90% to about 100% of the maximum heart rate of the subject.

In some embodiments, an exercise instruction of the disclosure is based upon a time of day. Non-limiting examples of times of day include early morning, mid-morning, afternoon, and evening. In some embodiments, the exercise instruction of the disclosure is based upon a diet consumed by the subject. In some embodiments, the exercise instruction of the disclosure is based upon an activity of the state of physical exercise. In some embodiments, the activity lowers the glucose level of the subject. In some embodiments, the activity raises the glucose level of the subject. If the subject chooses an exercise to perform, the system can modify the subject's insulin or glucagon administration rate based on the time of day, the selection of exercise, and other factors, such as heart rate and glucose levels.

Media-enhanced Exercise Instruction

A subject can receive exercise instruction for safe and effective activities for a diabetic. The subject can receive exercise instruction while using any device or system herein, or can receive exercise instruction without using any such device or system. Exercise instruction can be presented to the subject in any suitable format, for example, video, audio, email, text, in-person, presentation of words associated with an exercise instruction, presentation of sounds or symbols associated with an exercise instruction, group, one-on-one, and any combination thereof. Devices suitable for presenting exercise instruction include a media device, a communication medium, a video display device or unit, an audio device or unit, a device suitable for conveyance of email or text message, such as a computer, cellular telephone, or tablet, mannequins, posters, flyers, and any combination of the foregoing. In some embodiments, the subject inputs into the system a choice of exercise to perform, and receives instruction based on the subject's choice of exercise.

FIG. 1 illustrates a video for exercise instruction 100. The video for exercise instruction 100 comprises multimedia video content featuring exercise instruction and correlating presentation of diabetes metrics 101, including suggested heart rate zone 102; suggested perceived exertion rate 103; suggested glycogen depletion rate 104; potential blood glucose impact 105; suggested skeletal muscle usage 106; suggested metabolic pathway 107; amount of time per exercise 108; and name of exercise performed 109.

Video instruction for each exercise is presented on an electronic device to the subject in real time, and the subject can participate by performing or learning the exercise. Non-limiting examples of electronic devices include displays, computers, televisions, projectors, smartphones, smart watches, tablets, and electronic glasses. As the video for exercise instruction proceeds, and the instructor progresses through a series of exercises, information is displayed on the video output. Each exercise instruction is accompanied by the provision of suggested information related to desired results illustrated as side bars and popups in the video for exercise instruction.

Figure 2:
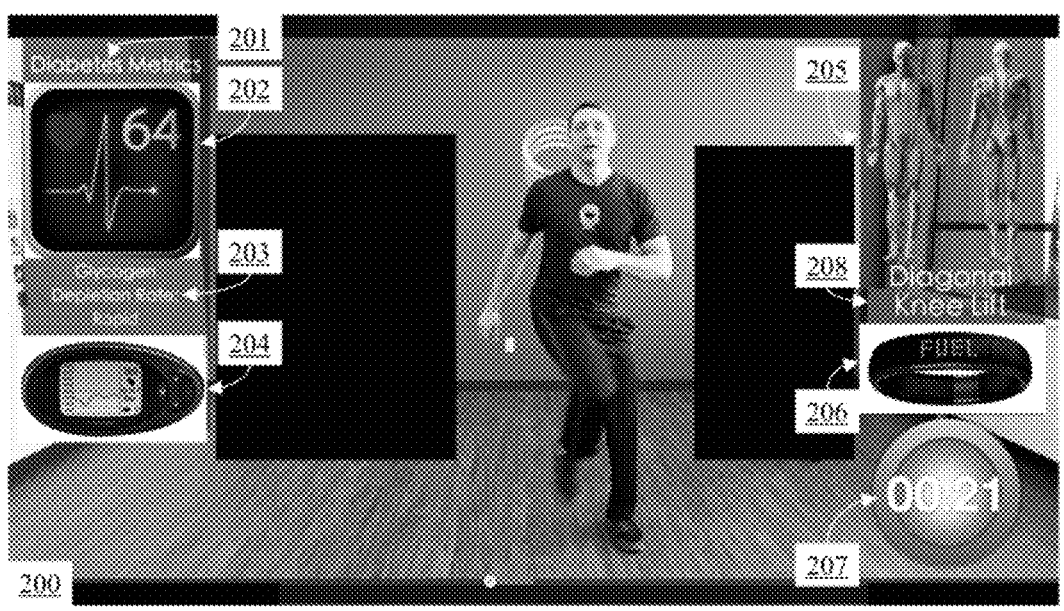
FIG. 2 illustrates an audiovisual data stream.

FIG. 2 illustrates a video for exercise instruction 200. The video for exercise instruction 200 comprises: multimedia video content featuring exercise instruction integrating content with software and devices that track bio-metric data related to diabetes and health metrics in real time. In this embodiment, the video for exercise instruction 200 combines the presentation of suggested data and information with the presentation of diabetes metrics 201 integrating real time bio-metric data, including active heart rate 202; suggested glycogen depletion rate 203; blood glucose level 204; suggested skeletal muscle usage 205; calorie expenditure and geospatial distance covered 206; amount of time per exercise 207; and name of exercise performed 208.

Bio-metric data can be incorporated and derived from software and wearable bio-metric tracking devices, and smartphone applications that track distance, speed, time and geography covered. These devices are worn by the subject, and monitor the signals of the subject. Data collected from these devices are transmitted to the system of the invention, which processes the data to provide a real-time display of data generated from the subject. The subject thus has the opportunity to observe and evaluate performance and compare output to recommended standards. The data can replace or supplement the suggested data, and are displayed in real time through Application Program Interface (API) protocols and BlueTooth™ integration.

Non-limiting examples of potential bio-metric data and smartphone application information include information derived from heart rate monitoring devices; information derived from external hormone delivery devices, such as insulin pumps and glucagon pumps; information derived from continuous glucose monitoring (CGM) devices; information derived from non-continuous glucose monitoring devices, such as blood glucose meters (BGMs); information derived from calorie expenditure devices; information derived from step counters; information derived from time and clock applications; information derived from metabolic pathway devices, such as New Leaf™ technology; and information derived from distance, speed and geospatial distance tracking devices, such as GPS technology.

In some embodiments, the disclosure herein provides methods for suggestive and responsive multimedia exercise instruction featuring, for example, a smartphone application that integrates exercise instruction and video content with bio-metric software and devices to make exercise suggestions based on desired diabetes metrics outcomes. Non-limiting examples of such outcomes include A1C reduction; A1C goal; increase in insulin sensitivity; decrease in insulin resistance; fat metabolism and weight loss; real-time lowering of blood glucose levels; real-time elevation of blood glucose levels; and reduction of anti-diabetic medication usage.

Utilizing the software, protocols, and algorithms described above, an application makes exercise suggestions based on factors geared towards exercise effective for a diabetes patient. Non-limiting examples of such factors include pre-exercise glucose levels; information derived from individual diabetes profile; established safety guidelines related to comorbidity conditions; real time feed-back from bio-metric devices; algorithms described herein; and categorization of exercise routines correlated with specific diabetes outcomes and conditions.

Figure 3:
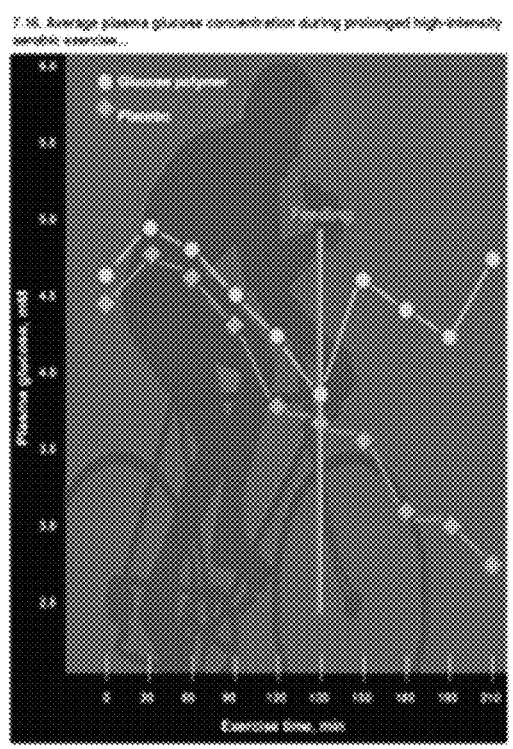
FIG. 3 depicts a system for delivering insulin.

FIG. 3 provides a graph tracking blood glucose level in millimolar (mM) over a period of exercise time in minutes (min) in individuals feeding themselves with either a placebo (diamonds) or a glucose polymer (circle) during prolonged, high-intensity aerobic exercise. Using the methods, systems, algorithms, computer program products, and computer-executable code of the disclosure for exercise guidance, glucose can be tracked over an exercise time course.

In some embodiments, an application platform disclosed herein provides a portal for subjects and providers to: input diabetes-specific bio-metric data such as glucose level, heart rate level and medication, such as manually via a smartphone application; receive specific and responsive exercise guidance based upon real-time data entry of diabetes-related bio-metric data, utilizing the clinical algorithms for exercise therapy; offer care providers a structured exercise program that can be both prescribed and reviewed; and integrate the algorithms and apps with wearable devices, bio-metric monitoring devices, and drug delivery devices to automate the input of diabetes-related bio-metric data and provide responsive exercise suggestions, based on the real-time flow of automated data.

The subject can have target ranges for various parameters, including biometric parameters and device parameters, such as dosage rates for insulin and glycogen administration devices. The target parameters can be pre-determined, prescribed, or determined by the subject, a health care profession, or a fitness professional. The system can alert the subject when a parameter deviates from a target range, for example, by audio, video, text, email, or by shutting down the exercise instruction program. The system can also modify the exercise program to instruct the subject to undertake activities likely to adjust the parameter back to the target range.

Integration of Diabetes Exercise Algorithms into Closed-loop Systems

Disclosed herein are methods, kits, systems, and devices incorporating algorithms for exercise guidance and instruction specific to diabetes relief and management into closed-loop or artificial pancreas systems. Such closed-loop systems include a device configured to monitor glucose levels and a device configured to deliver a compound to a subject. The loop begins with assessment of glucose levels in the subject. This assessment, if measured to be outside of a pre-determined range, is followed by transmission of a notification by the glucose monitoring device to the compound delivery device. This notification is followed by adjustment of the rate of compound delivery based upon the measured glucose level. The loop is closed by subsequent measurement of glucose levels by the glucose monitoring device.

In some embodiments, the disclosure provides methods for adjusting the interaction of the components of a closed-loop system based upon an exercise recommendation. In some embodiments, the rate of insulin delivery is decreased based upon the exercise recommendation. In some embodiments, the rate of insulin delivery is increased based upon the exercise recommendation. In some embodiments, the rate of glucagon delivery is decreased based upon the exercise recommendation. In some embodiments, the rate of glucagon delivery is increased based upon the exercise recommendation.

Figure 4:
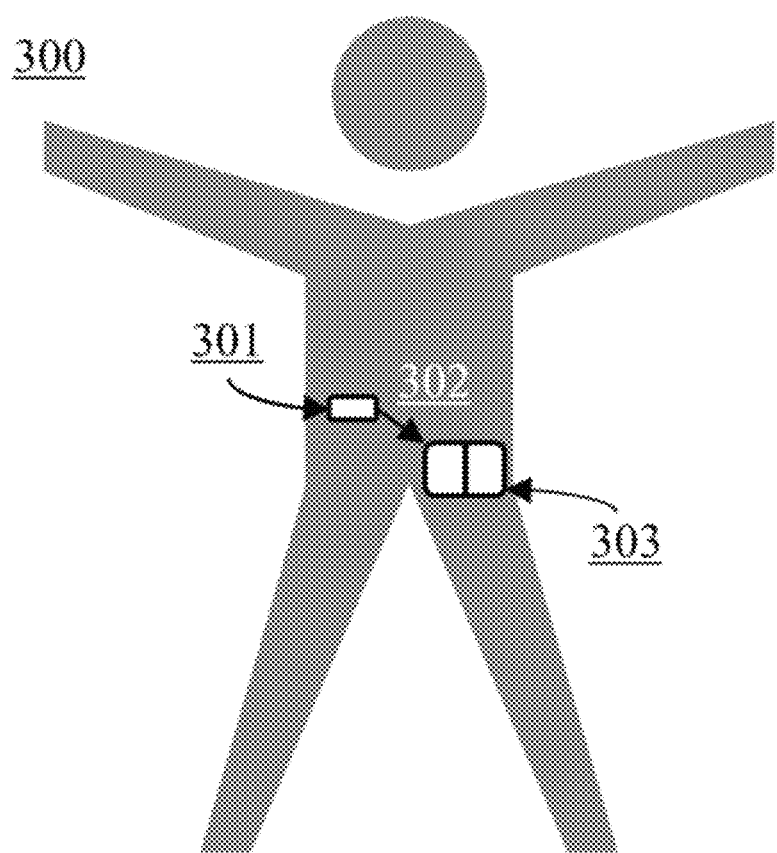
FIG. 4 depicts a system for delivering insulin.

FIG. 4 illustrates an embodiment of a closed-loop system 300 of the disclosure. The closed-loop system 300 comprises a continuous glucose monitor 301. When the continuous glucose monitor 301 measures a glucose value outside of a pre-determined range, the continuous glucose monitor 301 transmits a notification 302 to an insulin pump 303. The insulin pump 303 incorporates information relating to the exercise algorithms disclosed herein to adjust the insulin rate to return the glucose value to within an acceptable range based upon the calculated impact of the exercise activity on the glucose value. For example, if an exercise activity that would lower the blood glucose level, such as moderately paced hiking, was suggested by the algorithm, the closed-loop system 300 would account for this exercise activity to deliver a reduced rate of insulin to the subject.

Figure 5:
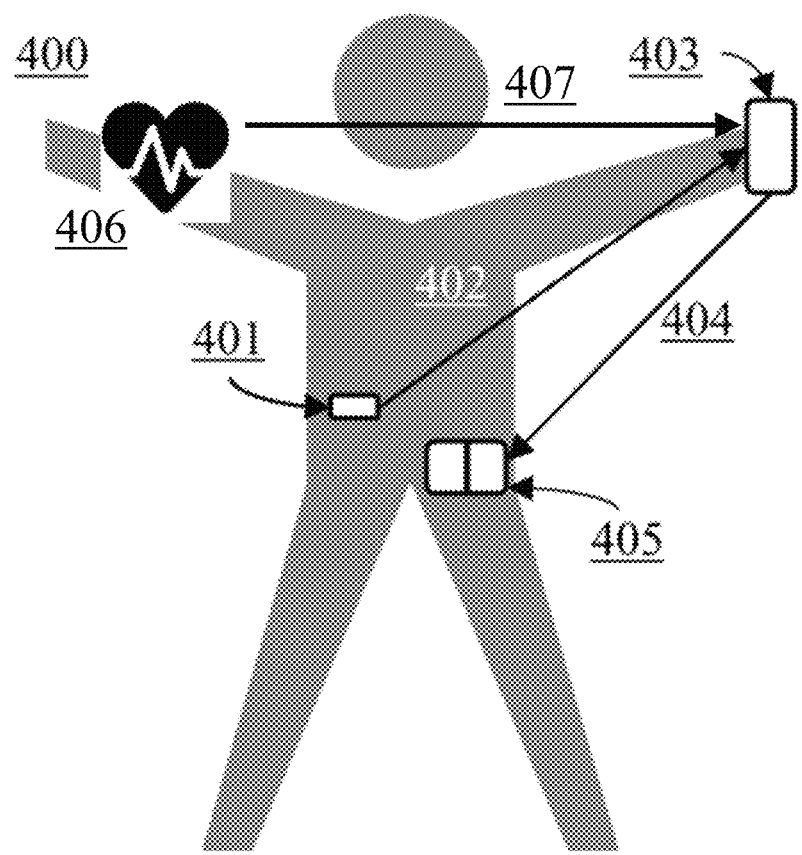
FIG. 5 depicts a graph of a plasma glucose concentration over exercise time.

FIG. 5 illustrates an embodiment of a closed-loop system 400 of the disclosure. The closed-loop system 400 comprises a continuous glucose monitor 401. When the continuous glucose monitor 401 measures a glucose value outside of a pre-determined range, the continuous glucose monitor 401 transmits a notification 402 to a telecommunications device with a processor, such as a smartphone 403. The telecommunications device 403 receives the notification 402 and incorporates the exercise algorithms disclosed herein to provide an instruction 404 to a dual insulin/glucagon pump 405. The dual insulin/glucagon pump 405 alters the rate of insulin and glucagon delivery to return the glucose value to within an acceptable range based upon the calculated impact of the exercise activity on the glucose value.

A heart rate monitor 406 is also in communication with telecommunications device 403. The heart rate monitor 406 can detect the subject's heart rate prior to, during, and after exercise, and communicate 407 the heart rate to telecommunications device 403. The heart rate that is communicated to telecommunications device 403 can influence the determination of other important factors, including the type of exercise instruction given to the subject, the dose of insulin to administer, the dose of glucagon to administer, whether to warn the subject of an unsafe circumstance, whether to advise the subject to consume a source of carbohydrates, or whether to terminate exercise.

For example, if an exercise activity that would raise the blood glucose level or alter heart rate, such as heavy weightlifting, was suggested by the algorithm, the closed-loop system 400 would account for this exercise activity to deliver an increased rate of insulin and decreased rate of glucagon to the subject.

In some embodiments, devices utilizing algorithms of the disclosure communicate instructions to, or receive instructions from, other devices as a component of a kit or system of the disclosure. All communications can be performed as disclosed herein, in the reverse, or in both directions.

In some embodiments, a glucose monitoring device, utilizing an algorithm of the disclosure, communicates an instruction to an insulin delivery device to administer insulin. In some embodiments, a glucose monitoring device, utilizing an algorithm of the disclosure, communicates an instruction to a glucagon delivery device to administer glucagon.

In some embodiments, a glucose monitoring device, utilizing an algorithm of the disclosure, communicates an instruction to a telecommunications device, which communicates the instruction to an insulin delivery device to administer insulin. In some embodiments, a glucose monitoring device, utilizing an algorithm of the disclosure, communicates an instruction to a telecommunications device, which communicates the instruction to a glucagon delivery device to administer glucagon. In some embodiments, a glucose monitoring device, utilizing an algorithm of the disclosure, communicates an instruction to a telecommunications device, which communicates the instruction to an insulin delivery device, which communicates the instruction to a glucagon delivery device to administer glucagon. In some embodiments, a glucose monitoring device, utilizing an algorithm of the disclosure, communicates an instruction to a telecommunications device, which communicates the instruction to a glucagon delivery device, which communicates the instruction to an insulin delivery device to administer insulin.

In some embodiments, a glucose monitoring device, utilizing an algorithm of the disclosure, communicates an instruction to an insulin delivery device, which communicates the instruction to a glucagon delivery device to administer glucagon. In some embodiments, a glucose monitoring device, utilizing an algorithm of the disclosure, communicates an instruction to a glucagon delivery device, which communicates the instruction to an insulin delivery device to administer insulin. In some embodiments, a glucose monitoring device, utilizing an algorithm of the disclosure, communicates an instruction to an insulin delivery device, which communicates the instruction to a telecommunications device, which communicates the instruction to a glucagon delivery device to administer glucagon. In some embodiments, a glucose monitoring device, utilizing an algorithm of the disclosure, communicates an instruction to a glucagon delivery device, which communicates the instruction to a telecommunications device, which communicates the instruction to an insulin delivery device to administer insulin.

In some embodiments, a telecommunications device, utilizing an algorithm of the disclosure, communicates an instruction to an insulin delivery device to administer insulin. In some embodiments, a telecommunications device, utilizing an algorithm of the disclosure, communicates an instruction to a glucagon delivery device to administer glucagon. In some embodiments, a telecommunications device, utilizing an algorithm of the disclosure, communicates an instruction to a glucose monitoring device to measure a glucose level. In some embodiments, a telecommunications device, utilizing an algorithm of the disclosure, communicates an instruction to a glucose monitoring device, which communicates the instruction to an insulin delivery device to administer insulin. In some embodiments, a telecommunications device, utilizing an algorithm of the disclosure, communicates an instruction to a glucose monitoring device, which communicates the instruction to a glucagon delivery device to administer glucagon.

In some embodiments, a telecommunications device, utilizing an algorithm of the disclosure, communicates an instruction to a glucose monitoring device, which communicates the instruction to an insulin delivery device, which communicates the instruction to a glucagon delivery device to administer glucagon. In some embodiments, a telecommunications device, utilizing an algorithm of the disclosure, communicates an instruction to a glucose monitoring device, which communicates the instruction to a glucagon delivery device, which communicates the instruction to an insulin delivery device to administer insulin. In some embodiments, a telecommunications device, utilizing an algorithm of the disclosure, communicates an instruction to an insulin delivery device, which communicates the instruction to a glucose monitoring device, which communicates the instruction to a glucagon delivery device to administer glucagon. In some embodiments, a telecommunications device, utilizing an algorithm of the disclosure, communicates an instruction to a glucagon delivery device, which communicates the instruction to a glucose monitoring device, which communicates the instruction to an insulin delivery device to administer insulin.

In some embodiments, a telecommunications device, utilizing an algorithm of the disclosure, communicates an instruction to a glucagon delivery device, which communicates the instruction to a glucose monitoring device to measure a glucose level. In some embodiments, a telecommunications device, utilizing an algorithm of the disclosure, communicates an instruction to an insulin delivery device, which communicates the instruction to a glucose monitoring device to measure a glucose level. In some embodiments, a telecommunications device, utilizing an algorithm of the disclosure, communicates an instruction to a glucagon delivery device, which communicates the instruction to an insulin delivery device, which communicates the instruction to a glucose monitoring device to measure a glucose level. In some embodiments, a telecommunications device, utilizing an algorithm of the disclosure, communicates an instruction to an insulin delivery device, which communicates the instruction to a glucagon delivery device, which communicates the instruction to a glucose monitoring device to measure a glucose level.

In some embodiments, a glucagon delivery device, utilizing an algorithm of the disclosure, communicates an instruction to an insulin delivery device to administer insulin. In some embodiments, a glucagon delivery device, utilizing an algorithm of the disclosure, communicates an instruction to a glucose monitoring device to measure a glucose level.

In some embodiments, a glucagon delivery device, utilizing an algorithm of the disclosure, communicates an instruction to a telecommunications device, which communicates the instruction to an insulin delivery device to administer insulin. In some embodiments, a glucagon delivery device, utilizing an algorithm of the disclosure, communicates an instruction to a telecommunications device, which communicates the instruction to a glucose monitoring device to measure a glucose level. In some embodiments, a glucagon delivery device, utilizing an algorithm of the disclosure, communicates an instruction to a telecommunications device, which communicates the instruction to an insulin delivery device, which communicates the instruction to a glucose monitoring device to measure a glucose level. In some embodiments, a glucagon delivery device, utilizing an algorithm of the disclosure, communicates an instruction to a telecommunications device, which communicates the instruction to a glucose monitoring device, which communicates the instruction to an insulin delivery device to administer insulin.

In some embodiments, a glucagon delivery device, utilizing an algorithm of the disclosure, communicates an instruction to an insulin delivery device, which communicates the instruction to a glucose monitoring device to measure a glucose level. In some embodiments, a glucagon delivery device, utilizing an algorithm of the disclosure, communicates an instruction to a glucose monitoring device, which communicates the instruction to an insulin delivery device to administer insulin. In some embodiments, a glucagon delivery device, utilizing an algorithm of the disclosure, communicates an instruction to an insulin delivery device, which communicates the instruction to a telecommunications device, which communicates the instruction to a glucose monitoring device to measure a glucose level. In some embodiments, a glucagon delivery device, utilizing an algorithm of the disclosure, communicates an instruction to a glucose monitoring device, which communicates the instruction to a telecommunications device, which communicates the instruction to an insulin delivery device to administer insulin.

In some embodiments, a glucagon delivery device, utilizing an algorithm of the disclosure, communicates an instruction to an insulin delivery device to administer insulin. In some embodiments, a glucagon delivery device, utilizing an algorithm of the disclosure, communicates an instruction to a glucose monitoring device to measure a glucose level.

In some embodiments, a glucagon delivery device, utilizing an algorithm of the disclosure, communicates an instruction to a telecommunications device, which communicates the instruction to an insulin delivery device to administer insulin. In some embodiments, a glucagon delivery device, utilizing an algorithm of the disclosure, communicates an instruction to a telecommunications device, which communicates the instruction to a glucose monitoring device to measure a glucose level. In some embodiments, a glucagon delivery device, utilizing an algorithm of the disclosure, communicates an instruction to a telecommunications device, which communicates the instruction to an insulin delivery device, which communicates the instruction to a glucose monitoring device to measure a glucose level. In some embodiments, a glucagon delivery device, utilizing an algorithm of the disclosure, communicates an instruction to a telecommunications device, which communicates the instruction to a glucose monitoring device, which communicates the instruction to an insulin delivery device to administer insulin.

In some embodiments, a glucagon delivery device, utilizing an algorithm of the disclosure, communicates an instruction to an insulin delivery device, which communicates the instruction to a glucose monitoring device to measure a glucose level. In some embodiments, a glucagon delivery device, utilizing an algorithm of the disclosure, communicates an instruction to a glucose monitoring device, which communicates the instruction to an insulin delivery device to administer insulin. In some embodiments, a glucagon delivery device, utilizing an algorithm of the disclosure, communicates an instruction to an insulin delivery device, which communicates the instruction to a telecommunications device, which communicates the instruction to a glucose monitoring device to measure a glucose level. In some embodiments, a glucagon delivery device, utilizing an algorithm of the disclosure, communicates an instruction to a glucose monitoring device, which communicates the instruction to a telecommunications device, which communicates the instruction to an insulin delivery device to administer insulin.

In some embodiments, an insulin delivery device, utilizing an algorithm of the disclosure, communicates an instruction to a glucagon delivery device to administer glucagon. In some embodiments, an insulin delivery device, utilizing an algorithm of the disclosure, communicates an instruction to a glucose monitoring device to measure a glucose level.

In some embodiments, an insulin delivery device, utilizing an algorithm of the disclosure, communicates an instruction to a telecommunications device, which communicates the instruction to a glucagon delivery device to administer glucagon. In some embodiments, an insulin delivery device, utilizing an algorithm of the disclosure, communicates an instruction to a telecommunications device, which communicates the instruction to a glucose monitoring device to measure a glucose level. In some embodiments, an insulin delivery device, utilizing an algorithm of the disclosure, communicates an instruction to a telecommunications device, which communicates the instruction to a glucagon delivery device, which communicates the instruction to a glucose monitoring device to measure a glucose level. In some embodiments, an insulin delivery device, utilizing an algorithm of the disclosure, communicates an instruction to a telecommunications device, which communicates the instruction to a glucose monitoring device, which communicates the instruction to a glucagon delivery device to administer glucagon.

In some embodiments, an insulin delivery device, utilizing an algorithm of the disclosure, communicates an instruction to a glucagon delivery device, which communicates the instruction to a glucose monitoring device to measure a glucose level. In some embodiments, an insulin delivery device, utilizing an algorithm of the disclosure, communicates an instruction to a glucose monitoring device, which communicates the instruction to a glucagon delivery device to administer glucagon. In some embodiments, an insulin delivery device, utilizing an algorithm of the disclosure, communicates an instruction to a glucagon delivery device, which communicates the instruction to a telecommunications device, which communicates the instruction to a glucose monitoring device to measure a glucose level. In some embodiments, an insulin delivery device, utilizing an algorithm of the disclosure, communicates an instruction to a glucose monitoring device, which communicates the instruction to a telecommunications device, which communicates the instruction to a glucagon delivery device to administer glucagon.

Figure 6:
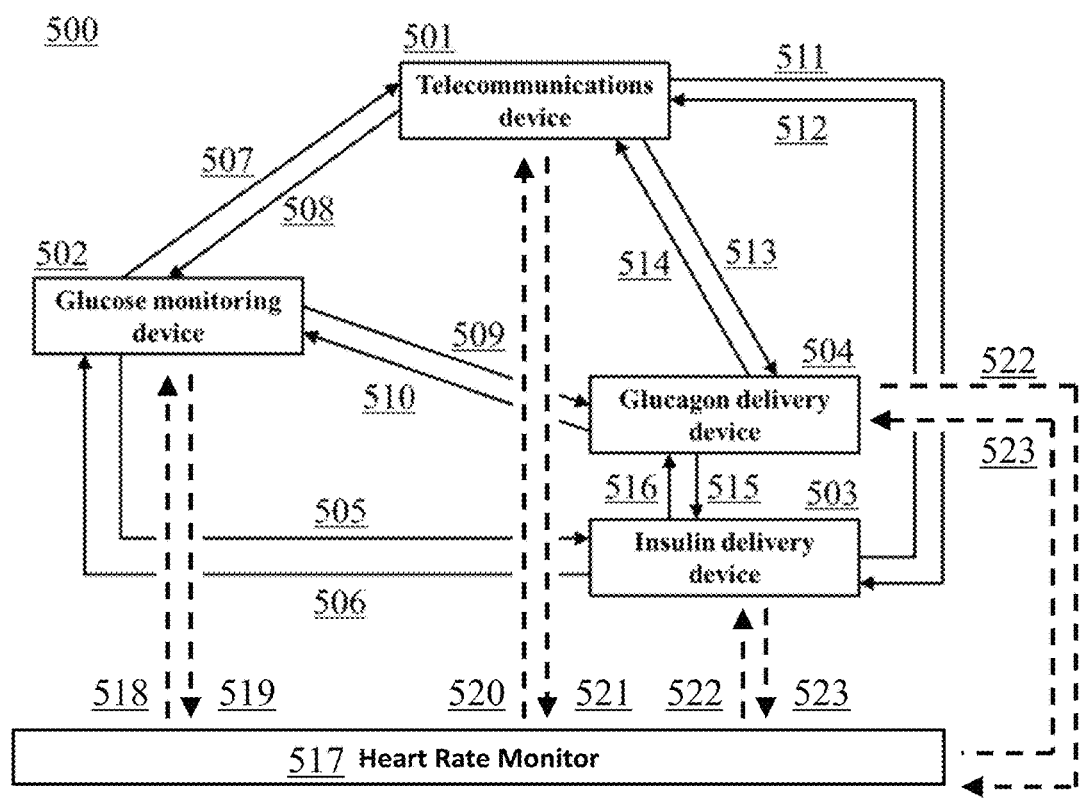
FIG. 6 depicts a closed-loop system.

FIG. 6 depicts communications among components of a closed-loop system 500. The closed-loop system 500 includes a telecommunications device 501, a glucose monitoring device 502, an insulin delivery device 503, and a glucagon delivery device 504. The glucose monitoring device 502, utilizing an algorithm of the disclosure, can transmit an instruction 505 to the insulin delivery device 503, and the insulin delivery device 503, utilizing an algorithm of the disclosure, can transmit an instruction 506 to the glucose monitoring device 502. The glucose monitoring device 502 can transmit an instruction 507, utilizing an algorithm of the disclosure, to the telecommunications device 501, and the telecommunications device 501, utilizing an algorithm of the disclosure, can transmit an instruction 508 to the glucose monitoring device 502. The glucose monitoring device 502 can transmit an instruction 509, utilizing an algorithm of the disclosure, to the glucagon delivery device 504, and the glucagon delivery device 504, utilizing an algorithm of the disclosure, can transmit an instruction 510 to the glucose monitoring device 502. The telecommunications device 501, utilizing an algorithm of the disclosure, can transmit an instruction 511 to the insulin delivery device 503, and the insulin delivery device 503, utilizing an algorithm of the disclosure, can transmit an instruction 512 to the telecommunications device 501. The telecommunications device 501 can transmit an instruction 513, utilizing an algorithm of the disclosure, to the glucagon delivery device 504, and the glucagon delivery device 504, utilizing an algorithm of the disclosure, can transmit an instruction 514 to the telecommunications device 501. The insulin delivery device 503 can transmit an instruction 515, utilizing an algorithm of the disclosure, to the glucagon delivery device 504, and the glucagon delivery device 504, utilizing an algorithm of the disclosure, can transmit an instruction 516 to the insulin delivery device 503. Any or all of the components of the system can be present in a single housing. Any or all of the components, or the single housing can be implantable or implanted in the subject.

FIG. 6 further depicts a heart rate monitor 517, connected to the other components by dashed lines. The heart rate monitor 517, utilizing an algorithm of the disclosure, can transmit an instruction 522 to the insulin delivery device 503, and the insulin delivery device 503, utilizing an algorithm of the disclosure, can transmit an instruction 523 to the heart rate monitor 517. The heart rate monitor 517 can transmit an instruction 520, utilizing an algorithm of the disclosure, to the telecommunications device 501, and the telecommunications device 501, utilizing an algorithm of the disclosure, can transmit an instruction 521 to the heart rate monitor 517. The heart rate monitor 517 can transmit an instruction 523, utilizing an algorithm of the disclosure, to the glucagon delivery device 504, and the glucagon delivery device 504, utilizing an algorithm of the disclosure, can transmit an instruction 522 to the heart rate monitor 517. The heart rate monitor 517 can transmit an instruction 518, utilizing an algorithm of the disclosure, to the glucose monitoring device 502, and the glucose monitoring device 502, utilizing an algorithm of the disclosure, can transmit an instruction 519 to the heart rate monitor 517. Any or all of the components of the system can be present in a single housing. Any or all of the components, or the single housing can be implantable or implanted in the subject.

Computer Processing for Diabetes Exercise Algorithms

Figure 7:
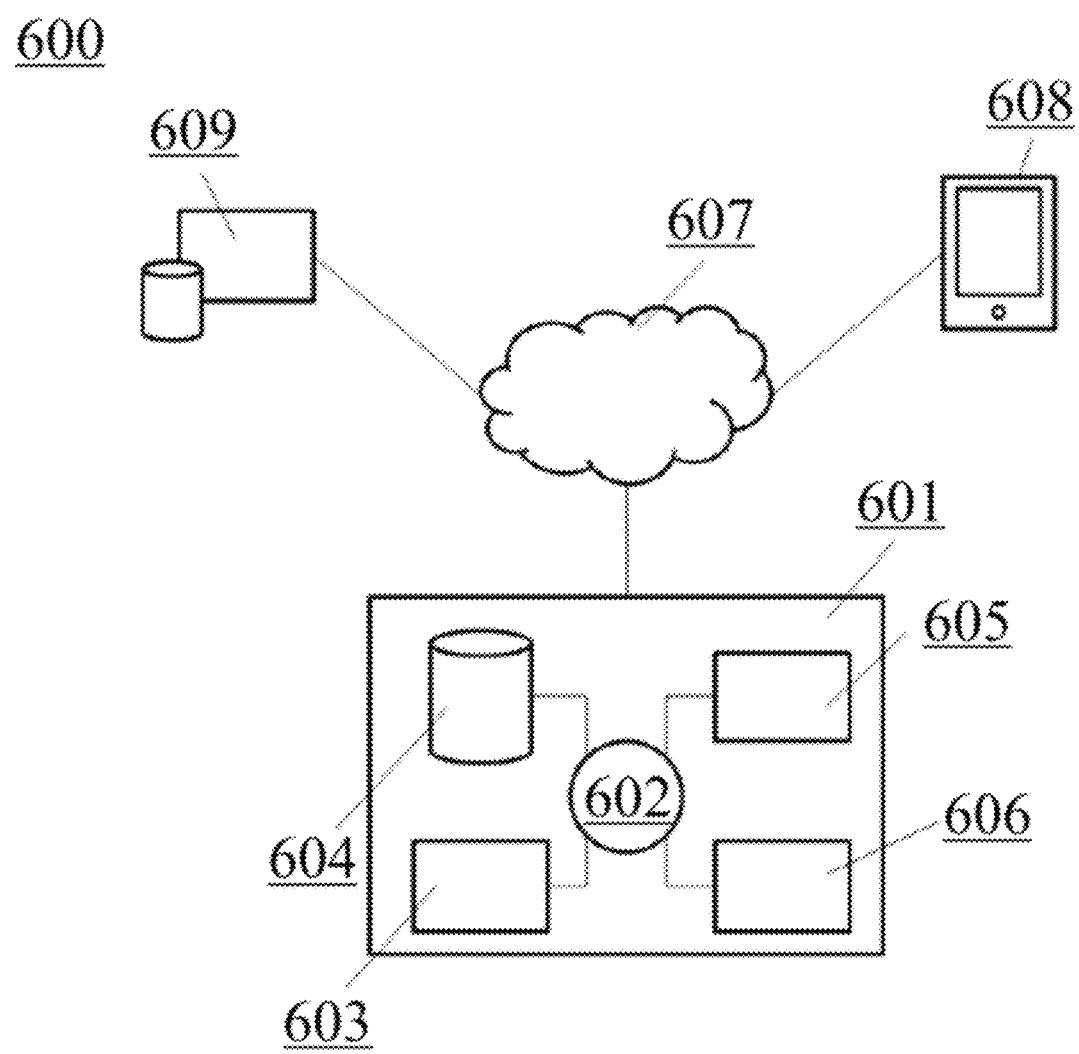
FIG. 7 illustrates a computer system for facilitating methods, systems, kits, or devices of the disclosure.

FIG. 7 shows a computer system 600 programmed or otherwise configured to allow a subject to monitor a glucose level and transmit a reading of the glucose level; to instruct administration of hormone to the subject; to instruct a state of physical exercise through an exercise instructional video; to display a reading of a biometric data of the subject; or to instruct an exercise instructional video to stop and to present an alternative exercise instructional video, in accordance with various embodiments of the present disclosure. The system 600 includes a computer server ("server") 601 that is programmed to implement methods disclosed herein. The server 601 includes a central processing unit 602, which can be a single core or multi core processor, or a plurality of processors for parallel processing. The server 601 also includes: memory 603, such as random-access memory, read-only memory, and flash memory; electronic storage unit 604, such as a hard disk; communication interface 605, such as a network adapter, for communicating with one or more other systems; and peripheral devices 606, such as cache, other memory, data storage and electronic display adapters. The memory 603, storage unit 604, interface 605 and peripheral devices 606 are in communication with the CPU 602 through a communication bus, such as a motherboard. The storage unit 604 can be a data storage unit or data repository for storing data. The server 601 can be operatively coupled to a computer network (hereinafter "network") 607 with the aid of the communication interface 605. The network 607 can be the Internet, an internet or extranet, or an intranet or extranet that is in communication with the Internet. The network 607 in some cases is a telecommunications network or data network. The network 607 can include one or more computer servers, which can allow distributed computing, such as cloud computing. The network 607, in some cases with the aid of the server 601, can implement a peer-to-peer network, which can allow devices coupled to the server 601 to behave as a client or an independent server.

The storage unit 604 can store files, such as files related to biometric data, glucose level readings, basal and adjusted rates of hormone administration, body weight, time of day of physical exercise, type of physical exercise, and duration of physical exercise. The storage unit 604 can store media items, such as exercise instruction videos of the disclosure. The storage unit 604 can store subject data, such as biometric data, glucose level readings, basal and adjusted rates of hormone administration, body weight, time of day of physical exercise, type of physical exercise, and duration of physical exercise at various points in time. The server 601 in some cases can include one or more additional data storage units that are external to the server 601, such as located on a remote server that is in communication with the server 601 through an intranet or the Internet. The storage unit 604 can store videos that provide exercise instruction, as well as items included in videos that provide exercise instruction, such as real-time biometric data collected during the performance of physical exercise with the video.

The server 601 can communicate with one or more remote computer systems through the network 607. In some embodiments, the server 601 is in communication with a first computer system 608 and a second computer system 609 that are located remotely with respect to the server 501. The first computer system 608 can be the computer system of a first subject, and the second computer system 609 can be that of a second subject, such as a personal trainer or third-party healthcare provider, such as a doctor, a nurse, or a dietician. The first computer system 608 and second computer system 609 can be, for example, personal computers, such as a portable PC; slate and tablet PC, such as Apple® iPad and Samsung® Galaxy Tab; telephones; smartphones, such as Apple® iPhone, Android-enabled device, Windows® Phone, and Blackberry®; smart watches, such as Apple® Watch; smart glasses, such as Google® Glass; or personal digital assistants. The first or second subject can access the server 601 via the network 607 to view or manage an exercise instruction video.

In some situations, the system 600 includes a single server 601. In other situations, the system 600 includes multiple servers in communication with one another through an intranet or the Internet. The server 601 can be adapted to store subject profile information, such as, for example, a name, physical address, email address, telephone number, instant messaging (IM) handle, educational information, work information, social likes or dislikes and historical information, such as information that can relate to the progress of a subject in exercise instruction, and other information of potential relevance to the subject. Such profile information can be stored on the storage unit 604 of the server 601.

Methods as described herein can be implemented by way of a machine- or computer-executable code or software stored on an electronic storage location of the server 601, such as, for example, on the memory 603 or electronic storage unit 604. During use, the code can be executed by the processor 602. In some cases, the code can be retrieved from the storage unit 604 and stored on the memory 603 for ready access by the processor 602, for example, computer-executable code for hormone administration while a subject is in a state of physical rest prior to the subject being in a state of physical exercise. In some situations, the electronic storage unit 604 can be precluded, and machine-executable instructions are stored on memory 603. Alternatively, the code can be executed on the second computer system 609. The code can be pre-compiled and configured for use with a processor adapted to execute the code, or can be compiled during runtime. The code can be supplied in a programming language that can be selected to allow the code to execute in a precompiled or as-compiled fashion.

All or portions of the software can at times be communicated through the Internet or various other telecommunications networks. Such communications can support loading of the software from one computer or processor into another, for example, from a management server or host computer into the computer platform of an application server. Another type of media that can bear the software elements includes optical, electrical and electromagnetic waves, such as those used across physical interfaces between local devices, through wired and optical landline networks and over various air-links. The physical elements that carry such waves, such as wired or wireless links, or optical links, also can be considered as media bearing the software.

A machine-readable medium, incorporating computer-executable code, can take many forms, including a tangible storage medium, a carrier wave medium, and physical transmission medium. Non-limiting examples of non-volatile storage media include optical disks and magnetic disks, such as any of the storage devices in any computer, such as can be used to implement the databases of FIG. 7. Volatile storage media include dynamic memory, such as a main memory of such a computer platform. Tangible transmission media include coaxial cables, copper wire and fiber optics, including wires that comprise a bus within a computer system. Carrier-wave transmission media can take the form of electric or electromagnetic signals, or acoustic or light waves such as those generated during radio frequency (RF) and infrared (IR) data communications.

Common forms of computer-readable media include: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, and any other medium from which a computer can read programming code or data. Many of these forms of computer readable media can be involved in carrying one or more sequences of one or more instructions to a processor for execution.

The server 601 can be configured for: data mining; extract, transform and load (ETL); or spidering operations, including Web Spidering where the system retrieves data from remote systems over a network and access an Application Programming Interface or parses the resulting markup, which can permit the system to load information from a raw data source or mined data into a data warehouse. The data warehouse can be configured for use with a business intelligence system, such as Microstrategy® and Business Objects®. The system can include a data mining module adapted to search for media items in various source locations, such as email accounts and various network sources, such as social networking accounts, such as Facebook®, Foursquare®, Google+®, and Linkedin®, or on publisher sites, such as weblogs.

An exercise instruction video can be presented to a subject on a subject interface (UI) of an electronic device of the subject. Non-limiting examples of UIs include a graphical subject interface (GUI) and web-based subject interface. A GUI can allow a subject to access an exercise instruction video. The GUI can allow a subject to edit the exercise instruction video, such as upload items to the exercise instruction video to display to other subjects in a manner selected by the subject. The UI, such as GUI, can be provided on a display of an electronic device of the subject. The display can be a capacitive or resistive touch display, or a head-mountable display, such as a Google® Glass. Such displays can be used with other systems and methods of the disclosure.

Methods of the disclosure can be facilitated with the aid of applications, or apps, that can be installed on an electronic device of the subject. An app can include a GUI on a display of the electronic device of the subject. The app can be programmed or otherwise configured to perform various functions of the system, such as, for example, permitting a subject to manage, such as create and edit, an exercise instructional program. GUIs of apps can display on an electronic device of the subject. Non-limiting examples of electronic devices include computers, televisions, smartphones, tablets, and smart watches. The electronic device can include, for example, a passive screen, a capacitive touch screen, or a resistive touch screen. The electronic device can include a network interface and a browser that allows the subject to access various sites or locations, such as web sites, on an intranet or the Internet. The app is configured to allow the mobile device to communicate with a server, such as the server 601.

Diabetes Exercise Algorithm Integration into External Devices

Methods, systems, kits, and devices of the disclosure can incorporate diabetes exercise algorithms into external devices. Non-limiting examples of external devices that can incorporate diabetes exercise algorithms include external insulin delivery devices, external glucagon delivery devices, and external glucose monitoring devices.

In some embodiments, the subject receives or is administered the dose of hormone through an external hormone delivery device in contact with the subject. In some embodiments, the external hormone delivery device is configured to pump hormone. In some embodiments, the external hormone delivery device is configured to inject hormone. In some embodiments, the external insulin delivery device and external glucagon delivery device are contained within a common housing.

In some embodiments, a hormone pump is capable of automatic injection a fixed amount of hormone at defined rates or time points by driving a piston in a state where an injection needle is inserted into a body fat region of the abdomen of the subject. In the pump, an injector is mounted on a side of a box-type housing in a longitudinal direction, and a push member is mounted at a lower section of the injector to drive the injector. The injector includes a cylindrical syringe for containing hormone therein and a piston inserted into the syringe for pushing the hormone through a tube. A disk-type push member is mounted on the lower end of the piston, and a female screw is formed at the center of the push member.

A motor and a power supply, which has a number of deceleration gear lines for decelerating a rotational speed of the motor, are mounted on the lower portion of the box-type housing, and a rotary shaft is mounted on a final gear of the deceleration gear lines. The rotary shaft has a male screw of the circumferential surface thereof, and the male screw is coupled with the female screw of the push member. As a result, the push member advances according to the rotation of the rotary shaft, the piston advances inside the syringe, and thereby, the hormone corresponding to an advanced amount of the piston is injected into the subject through the tube and an injection needle. In some embodiments, the hormone pump includes a cover to allow the injector to be drawn to the outside of the box-type housing when the hormone is loaded into the pump. In some embodiments, the hormone pump includes a connector for connecting the tube to the syringe. In some embodiments, the hormone pump includes a sealing cap for preventing penetration of moisture into the power supply.

In some embodiments, the subject measures a glucose level of the subject through an external glucose monitoring device in contact with the subject. In some embodiments, the external glucose monitoring device is a glucose meter device. In some embodiments, the external glucose monitoring device is a continuous glucose monitoring device. In some embodiments, the continuous glucose monitoring device is implanted underneath the skin.

Two major classes of glucose monitoring devices are used by subjects: (1) non-continuous or single-point glucose monitoring devices, such as blood glucose meters and blood glucose test strips; and (2) continuous glucose monitoring devices. Non-continuous glucose monitoring devices consist of meters and test strips that require blood samples to be drawn from fingertips, forearms, or legs. These glucose monitoring devices rely on lancing and manipulation of the blood draw site.

Continuous glucose monitoring devices are implanted, for example, subcutaneously, and measure glucose levels in the interstitial fluid at various time points throughout the day, to show trends in glucose levels over a period of time. As these devices are implanted, use of a continuous glucose monitoring devices requires the assistance of a health care professional. Continuous glucose monitoring devices also require frequent, for example, daily calibration using blood glucose results obtained from non-continuous glucose monitoring devices. This repeated calibration is necessary to maintain sensor accuracy and sensitivity.

In some embodiments, a continuous glucose monitoring device has an array of hollow microneedles or other tissue piercing elements extending through the stratum corneum of a subject into the interstitial fluid beneath the stratum corneum. The microneedles in the array are hollow and have open distal ends, and their interiors communicate with a sensing area within a sensor channel. The sensing area is therefore in fluid communication with interstitial fluid through the microneedle array. The sensing area and the microneedle array are pre-filled with sensing fluid prior to the first use of the device. Thus, when the device is implanted into the skin of the subject and the microneedles pierce the stratum corneum of the skin, substantially no net fluid transfers from the interstitial fluid into the microneedles, but instead glucose diffuses from the interstitial fluid into the sensing fluid within the needles.

Disposed above and in fluid communication with sensor channel is a glucose sensor. In some embodiments, the glucose sensor is an electrochemical glucose sensor that generates an electrical signal, such as current, voltage and charge, whose value depends on the concentration of glucose in the fluid within the sensing area. A sensor electronics element receives the voltage signal from the glucose sensor. In some embodiments, the sensor electronics element uses the sensed signal to compute a glucose concentration and display it. In other embodiments, sensor electronics element transmits the sensed signal, or information derived from the sensed signal, to a remote device, such as through wireless communication. The continuous glucose monitoring device is held in place on the skin by one or more adhesive pads.

In some embodiments, the continuous glucose monitoring device has a built-in sensor calibration system. A reservoir comprises a sensing fluid with, for example, a glucose concentration from about 1 mg/dL to about 400 mg/dL. In some embodiments, the glucose concentration in the sensing fluid is selected to be below the glucose sensing range of the sensor. The sensing fluid can comprise buffers, preservatives, or other substances in addition to glucose. Upon actuation of a manual or automatic pump, plunger or other actuator, sensing fluid is forced from the reservoir through a first check valve, such as a flap valve, into a sensing channel. The sensing fluid within the sensing channel is forced through a second check valve, such as a flap valve, into a waste reservoir. Check valves or similar gating systems are used to reduce the likelihood of contamination. Because the fresh sensing fluid has a known glucose concentration, the sensor is calibrated at this value to set a baseline. After calibration, the sensing fluid in the sensing channel remains stationary, and glucose from the interstitial fluid diffuses through microneedles into the sensing area. Changes in the glucose concentration over time reflect differences between the calibration glucose concentration of the sensing fluid in the reservoir and the glucose concentration of the interstitial fluid, which can be correlated with the actual blood glucose concentration of the subject. Because of possible degradation of the sensor or loss of sensor sensitivity over time, the continuous glucose monitoring device can be periodically recalibrated by manual or automatic operation of the actuator to send fresh sensing fluid from the reservoir into the sensing area.

In some embodiments, the glucose monitoring device can measure other analytes, such as electrolytes, for example, sodium, calcium, magnesium, zinc, iron, and potassium. In some embodiments, the glucose monitoring device can use any suitable sensor including, for example, an electrochemical sensor and an optical sensor.

EXAMPLES

Example 1

Use of Algorithms for Diabetes Exercise Therapy to Improve Diabetic Outcomes

A subject was a 52 year-old male diagnosed with type 2 diabetes for about 8 years. Prior to beginning the exercise therapy, the subject was on a combination anti-diabetic therapy comprising injection with insulin. The subject engaged in exercise guidance based on the methods disclosed herein, including exercise suggestions based on desired diabetes metrics outcomes, including A1C reduction, weight loss, and reduction of anti-diabetic medication usage. Having engaged the exercises based on the methods disclosed herein, the subject achieved several diabetes metrics outcomes, including: a reduction of A1C from about 9.3% to about 6.0%; a weight loss of 58 pounds; and a reduction of insulin therapy from 116 units per day to about 59 units per day.

Example 2

Use of Algorithms for Diabetes Exercise Therapy to Improve Diabetic, Cardiovascular, and Pulmonary Outcomes A subject was an elderly male that was diagnosed with type 2 diabetes and required an oxygen tank for breathing.

Several years prior to beginning the exercise therapy, the subject had experienced substantial liver failure that limited the ability of the subject to exercise. The subject engaged in exercise guidance based on the methods disclosed herein, including exercise suggestions based on desired diabetic, cardiovascular, and pulmonary outcomes and capacities of the subject. Having engaged the exercises based on the methods disclosed herein, the subject achieved several desired outcomes, including: increased muscle tone; increased cardiac stress resistance; and increased lung function.

Example 3

Use of Algorithms for Design of Targeted Type 1 Diabetes Exercise Therapy and Insulin Administration A subject is a 31 year-old female diagnosed with type 1 diabetes for 26 years. The subject measures a glucose level with a continuous glucose monitoring device and enters a resting glucose level reading into the application. The resting glucose level is 128 mg/dL. The subject selects a desired diabetes outcome in the application of A1C goal. The subject receives instruction for an exercise routine to be performed in a gym based upon weight lifting selected to create an active heart rate from 90% to 100% of the maximum heart rate of the subject. The maximum heart rate was estimated by subtracting the age of the subject from 220, to yield a maximum heart rate of 188 beats per minute (bpm).

As the instructed, exercise routine creates an active heart rate from 90% to 100% of the maximum heart rate of the subject, which increases the glucose level of the subject, the application suggests adjusting the dose of insulin from a basal rate of 1 unit per hour (U/h) to an adjusted rate of 1.2 U/h. The application further utilizes real-time data from bio-metric devices, including a heart rate monitor and the continuous glucose monitoring device, to make further suggestions in real time related to the desired diabetes outcome, including changes in routine, and warnings to stop and or test blood sugar, or changes in hormone administration.

Example 4

Use of Algorithms for Real-Time Tracking of Type 2 Diabetes Exercise Therapy

A subject is a 47 year-old female diagnosed with type 2 diabetes for 3 years. The subject is currently taking the oral medication metformin. The subject measures a glucose level with a single-point glucose monitoring device and enters a resting glucose level reading into the application. The resting glucose level is 150 mg/dL. The subject selects a desired diabetes outcome in the application of real-time reduction of blood glucose levels. The subject enters a critical glucose range of 100 mg/dL to 250 mg/dL. The subject receives instruction for a lower body cardiovascular exercise, such as jogging on a treadmill; cycling on a stationary bicycle; or running on an elliptical, utilizing slow twitch muscle fibers for 25 minutes. The exercise routine is selected to create an active heart rate from 60% to 70% of the maximum heart rate of the subject. The maximum heart rate was estimated by multiplying the age of the subject by 0.7 and subtracting the value from 208, to yield a maximum heart rate of 175.1 bpm. The application utilizes real-time data from bio-metric devices, including an activity tracker that monitors calorie expenditure and the single-point glucose monitoring device.

Based upon a reading of the glucose level from the single-point glucose monitoring device that the glucose level of the subject is below the critical glucose range, the application provides a warning to the subject in real time to stop the exercise routine and consume a carbohydrate to restore the glucose level to within the critical glucose range. Upon consumption of a fast-acting glucose chewable, the subject re-tests the glucose level with the single-point glucose monitoring device, which is transmitted to the application. Upon reading of the glucose level within the critical glucose range, the application suggests continuing the brisk walk with continued monitoring of the glucose level.

Example 5

Use of Algorithms for Real-Time Modification of Type 2 Diabetes Exercise Therapy A subject is a 52 year-old male diagnosed with type 2 diabetes for 7 years. The subject has previously performed several exercise routines based upon the suggestions of the application. The subject measures a glucose level with a blood glucose meter and enters a resting glucose level reading into the application. The resting glucose level is 110 mg/dL. The subject selects a desired diabetes outcome in the application of increased fat metabolism. The subject receives instruction from the application for an exercise routine based on high-intensity interval training combined with weight lifting selected to create an active heart rate from 90% to 100% of the maximum heart rate of the subject. The maximum heart rate of the subject has previously been measured through the treadmill test to be 172 bpm.

The application utilizes real-time data from bio-metric devices, including a heart rate monitoring device and the blood glucose meter. Based upon a reading of the glucose level from the blood glucose meter that the glucose level of the subject is above the critical glucose range of 100 mg/dL to 140 mg/dL, the application provides a warning to the subject in real time to stop the current exercise routine of high-intensity interval training combined with weight lifting. The application suggests an exercise routine based upon cycling on an exercise bicycle, along with re-testing of the glucose level with the blood glucose meter, to restore the glucose level to within the critical glucose range. The subject stops the current exercise routine of high-intensity interval training combined with weight lifting and begins the suggested exercise routine of cycling on the exercise bicycle. The subject further re-tests the glucose level with the blood glucose meter device, which is transmitted to the application. Upon reading of the glucose level within the critical glucose range, the application suggests returning to the initial exercise routine of high-intensity interval training combined with weight lifting, along with continued monitoring of the glucose level.

Example 6

Use of Algorithms for Type 1 Diabetes Exercise Therapy and Real-time Modification of Insulin and Glucagon Administration in a Closed-loop System A subject is a 28 year-old male diagnosed with type 1 diabetes for 23 years. The subject uses a closed-loop system including a continuous glucose monitoring device, a dual insulin/glucagon pump contained within a common housing, and a telecommunications device. The continuous glucose monitoring device transmits a resting glucose level reading into the application on the telecommunications device. The resting glucose level is 139 mg/dL. The subject selects a desired diabetes outcome in the application of A1C reduction. The subject receives instruction for an exercise routine to be performed with an exercise instruction video to reach a target heart rate from 60% to 70% of the maximum heart rate of the subject. The subject sets the critical glucose range to be from 100 mg/dL to 140 mg/dL. The maximum heart rate is estimated by subtracting the age of the subject from 220, to yield a maximum heart rate of 192 bpm.

As the instructed exercise routine creates an active heart rate from 60% to 70% of the maximum heart rate of the subject, which decreases the glucose level of the subject, the application suggests adjusting the dose of insulin from a basal rate of 1 U/h to an adjusted rate of 0.9 U/h and adjusting the dose of glucagon from a basal rate of 0.4 U/h to an adjusted rate of 0.5 U/h. The application further utilizes real-time data from the continuous glucose monitoring device of the closed-loop system and displays the glucose level readings with the exercise instruction video in real time. During the exercise instruction video, the glucose level rises above the critical glucose range, which is displayed on the exercise instruction video. The closed-loop system responds to the glucose level reading to increase the rate of the dose of insulin to 0.95 U/h and decrease the rate of the dose of glucagon to 0.45 U/h. The closed-loop system continues to monitor the glucose level with the continuous glucose monitoring device, transmitting the readings to the application and displaying the readings on the exercise instruction video.

EMBODIMENTS

Embodiment 101. A method comprising: a) administering to a subject a basal dose of insulin, wherein the subject is in need thereof, and wherein the subject is diabetic; b) subsequent to the administering to the subject the basal dose of insulin, administering to the subject an adjusted dose of insulin, wherein the adjusted dose of insulin is from about 5% to about 95% of the basal dose of insulin; c) subsequent to the administering to the subject the adjusted dose of insulin, sustaining the subject's heart rate at a level that is from 10%-50% of the subject's maximum heart rate for at least 30 minutes; and d) subsequent to the sustaining the subject's heart rate at the level that is from 10%-50% of the subject's maximum heart rate for at least 30 minutes, elevating the subject's heart rate to a level that is at least 50% of the subject's maximum heart rate.

Embodiment 102. The method of embodiment 101, wherein the subject has type 1 diabetes.

Embodiment 103. The method of embodiment 101, wherein the subject has type 2 diabetes.

Embodiment 104. The method of any one of embodiments 101-103, further comprising administering glucagon to the subject.

Embodiment 105. The method of any one of embodiments 101-104, wherein the adjusted dose of insulin is about 15% of the basal dose of insulin, and the subject's heart rate is elevated to 50-60% of the subject's maximum heart rate.

Embodiment 106. The method of any one of embodiments 101-104, wherein the adjusted dose of insulin is about 15% of the basal dose of insulin, and the subject's heart rate is elevated to 60-70% of the subject's maximum heart rate.

Embodiment 107. The method of any one of embodiments 101-104, wherein the adjusted dose of insulin is about 50% of the basal dose of insulin, and the subject's heart rate is elevated to 70-80% of the subject's maximum heart rate.

Embodiment 108. The method of any one of embodiments 101-104, wherein the adjusted dose of insulin is about 85% of the basal dose of insulin, and the subject's heart rate is elevated to 80-90% of the subject's maximum heart rate.

Embodiment 109. The method of any one of embodiments 101-104, wherein the adjusted dose of insulin is about 90% of the basal dose of insulin, and the subject's heart rate is elevated to 90-100% of the subject's maximum heart rate.

Embodiment 110. The method of any one of embodiments 101-109, wherein the basal dose of insulin and the adjusted dose of insulin are administered to the subject via an external medical device.

Embodiment 111. The method of any one of embodiments 101-110, wherein the basal dose of insulin and the adjusted dose of insulin are administered to the subject via an insulin pump.

Embodiment 112. The method of any one of embodiments 101-111, wherein the subject's heart rate is sustained at a level that is from 10%-50% of the subject's maximum heart rate for at least 60 minutes.

Embodiment 113. The method of any one of embodiments 101-112, wherein the subject's heart rate is sustained at a level that is from 10%-50% of the subject's maximum heart rate by promoting a state of physical rest for the subject.

Embodiment 114. The method of any one of embodiments 101-113, wherein the subject's heart rate is elevated to a level that is at least 50% of the subject's maximum heart rate by promoting a state of physical exercise for the subject.

Embodiment 115. The method of any one of embodiments 101-113, wherein the subject's heart rate is elevated to a level that is at least 50% of the subject's maximum heart rate by promoting a state of physical exercise for the subject, wherein the state of physical exercise is promoted by presenting to the subject an exercise instruction via an electronic communication medium.

Embodiment 116. The method of any one of embodiments 101-113, wherein the subject's heart rate is elevated to a level that is at least 50% of the subject's maximum heart rate by promoting a state of physical exercise for the subject, wherein the state of physical exercise is promoted by presenting to the subject an exercise instruction via an electronic communication medium, wherein the electronic communication medium is processed by a computer system that is in communication with a biometric device that is in contact with the subject.

Embodiment 117. The method of any one of embodiments 101-113, wherein the subject's heart rate is elevated to a level that is at least 50% of the subject's maximum heart rate by promoting a state of physical exercise for the subject, wherein the state of physical exercise is promoted by presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; and 2) displays the reading of the biometric parameter on the electronic communication medium.

Embodiment 118. The method of any one of embodiments 101-113, wherein the subject's heart rate is elevated to a level that is at least 50% of the subject's maximum heart rate by promoting a state of physical exercise for the subject, wherein the state of physical exercise is promoted by presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; and 2) determines based on the biometric parameter the suitability at the time point for the subject of an exercise instruction presented to the subject.

Embodiment 119. The method of any one of embodiments 101-113, wherein the subject's heart rate is elevated to a level that is at least 50% of the subject's maximum heart rate by promoting a state of physical exercise for the subject, wherein the state of physical exercise is promoted by presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; 2) determines based on the biometric parameter that an exercise instruction presented to the subject is unsuitable for the subject at the time point; 3) alerts the subject that the biometric parameter has deviated from a target range; 4) stops the presentation of the electronic communication medium; and 5) presents to the subject, based on the biometric parameter, an alternative electronic communication medium that provides an alternative exercise instruction that is suitable for the subject.

Embodiment 120. The method of any one of embodiments 116-119, wherein the biometric device monitors the subject's glucose level.

Embodiment 121. The method of any one of embodiments 116-120, wherein the biometric device monitors the subject's heart rate.

Embodiment 122. The method of any one of embodiment 115-121, wherein the electronic communication medium is a video.

Embodiment 201. A method comprising: a) administering to a subject a basal dose of insulin, wherein the subject is in need thereof, and wherein the subject is diabetic; b) receiving from the subject a selection of an exercise that the subject is to perform; c) determining based on the exercise that the subject is to perform an adjusted dose of insulin for administration to the subject, wherein the adjusted dose of insulin is from about 5% to about 95% of the basal dose of insulin; d) administering to the subject the adjusted dose of insulin; e) subsequent to the administering to the subject the adjusted dose of insulin, sustaining the subject's heart rate at a level that is from 10%-50% of the subject's maximum heart rate for at least 30 minutes; and f) subsequent to the sustaining the subject's heart rate at the level that is from 10%-50% of the subject's maximum heart rate for at least 30 minutes, monitoring the subject's heart rate to detect an elevation in the subject's heart rate, wherein the elevation in the subject's heart rate is to a level that is at least 50% of the subject's maximum heart rate.

Embodiment 202. The method of embodiment 201, wherein the subject has type 1 diabetes.

Embodiment 203. The method of embodiment 201, wherein the subject has type 2 diabetes.

Embodiment 204. The method of any one of embodiments 201-203, further comprising administering glucagon to the subject.

Embodiment 205. The method of any one of embodiments 201-204, wherein the adjusted dose of insulin is about 15% of the basal dose of insulin, and the elevation in the subject's heart rate is to 50-60% of the subject's maximum heart rate.

Embodiment 206. The method of any one of embodiments 201-204, wherein the adjusted dose of insulin is about 15% of the basal dose of insulin, and the elevation in the subject's heart rate is to 60-70% of the subject's maximum heart rate.

Embodiment 207. The method of any one of embodiments 201-204, wherein the adjusted dose of insulin is about 50% of the basal dose of insulin, and the elevation in the subject's heart rate is to 70-80% of the subject's maximum heart rate.

Embodiment 208. The method of any one of embodiments 201-204, wherein the adjusted dose of insulin is about 85% of the basal dose of insulin, and the elevation in the subject's heart rate is to 80-90% of the subject's maximum heart rate.

Embodiment 209. The method of any one of embodiments 201-204, wherein the adjusted dose of insulin is about 90% of the basal dose of insulin, and the elevation in the subject's heart rate is to 90-100% of the subject's maximum heart rate.

Embodiment 210. The method of any one of embodiments 201-209, wherein the basal dose of insulin and the adjusted dose of insulin are administered to the subject via an external medical device.

Embodiment 211. The method of any one of embodiments 201-209, wherein the basal dose of insulin and the adjusted dose of insulin are administered to the subject via an insulin pump.

Embodiment 212. The method of any one of embodiments 201-211, wherein the subject's heart rate is sustained at a level that is from 10%-50% of the subject's maximum heart rate for at least 60 minutes.

Embodiment 213. The method of any one of embodiments 201-212, wherein the subject's heart rate is sustained at a level that is from 10%-50% of the subject's maximum heart rate by promoting a state of physical rest for the subject.

Embodiment 214. The method of any one of embodiments 201-213, further comprising presenting to the subject an exercise instruction via an electronic communication medium.

Embodiment 215. The method of any one of embodiments 201-213, further comprising presenting to the subject an exercise instruction via an electronic communication medium, wherein the electronic communication medium is processed by a computer system that is in communication with a biometric device that is in contact with the subject.

Embodiment 216. The method of any one of embodiments 201-213, further comprising presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; and 2) displays the reading of the biometric parameter on the electronic communication medium.

Embodiment 217. The method of any one of embodiments 201-213, further comprising presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; and 2) determines based on the biometric parameter the suitability at the time point for the subject of an exercise instruction presented to the subject.

Embodiment 218. The method of any one of embodiments 201-213, further comprising presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; 2) determines based on the biometric parameter that an exercise instruction presented to the subject is unsuitable for the subject at the time point; 3) alerts the subject that the biometric parameter has deviated from a target range; 4) stops the presentation of the electronic communication medium; and 5) presents to the subject, based on the biometric parameter, an alternative electronic communication medium that provides an alternative exercise instruction that is suitable for the subject.

Embodiment 219. The method of any one of embodiments 215-218, wherein the biometric device monitors the subject's glucose level.

Embodiment 220. The method of any one of embodiments 215-218, wherein the biometric device monitors the subject's heart rate.

Embodiment 221. The method of any one of embodiments 214-220, wherein the electronic communication medium is a video.

Embodiment 301. A method comprising: a) receiving by a subject a basal dose of insulin, wherein the subject is in need thereof, and wherein the subject is diabetic; b) subsequent to the receiving the basal dose of insulin, receiving by the subject an adjusted dose of insulin, wherein the adjusted dose of insulin is from about 5% to about 95% of the basal dose of insulin; c) subsequent to the receiving by the subject the adjusted dose of insulin, sustaining by the subject the subject's heart rate at a level that is from 10%-50% of the subject's maximum heart rate for at least 30 minutes; and d) subsequent to the sustaining the subject's heart rate at the level that is from 10%-50% of the subject's maximum heart rate for at least 30 minutes, elevating by the subject the subject's heart rate to a level that is at least 50% of the subject's maximum heart rate.

Embodiment 302. The method of embodiment 301, wherein the subject has type 1 diabetes.

Embodiment 303. The method of embodiment 301, wherein the subject has type 2 diabetes.

Embodiment 304. The method of any one of embodiments 301-303, further comprising receiving a dose of glucagon by the subject.

Embodiment 305. The method of any one of embodiments 301-304, wherein the adjusted dose of insulin is about 15% of the basal dose of insulin, and the subject's heart rate is elevated to 50-60% of the subject's maximum heart rate.

Embodiment 306. The method of any one of embodiments 301-304, wherein the adjusted dose of insulin is about 15% of the basal dose of insulin, and the subject's heart rate is elevated to 60-70% of the subject's maximum heart rate.

Embodiment 307. The method of any one of embodiments 301-304, wherein the adjusted dose of insulin is about 50% of the basal dose of insulin, and the subject's heart rate is elevated to 70-80% of the subject's maximum heart rate.

Embodiment 308. The method of any one of embodiments 301-304, wherein the adjusted dose of insulin is about 85% of the basal dose of insulin, and the subject's heart rate is elevated to 80-90% of the subject's maximum heart rate.

Embodiment 309. The method of any one of embodiments 301-304, wherein the adjusted dose of insulin is about 90% of the basal dose of insulin, and the subject's heart rate is elevated to 90-100% of the subject's maximum heart rate.

Embodiment 310. The method of any one of embodiments 301-309, wherein the subject receives the basal dose of insulin and the adjusted dose of insulin via an external medical device.

Embodiment 311. The method of any one of embodiments 301-309, wherein the subject receives the basal dose of insulin and the adjusted dose of insulin via an insulin pump.

Embodiment 312. The method of any one of embodiments 301-311, wherein the subject's heart rate is sustained at a level that is from 10%-50% of the subject's maximum heart rate for at least 60 minutes.

Embodiment 313. The method of any one of embodiments 301-312, wherein the subject's heart rate is sustained at a level that is from 10%-50% of the subject's maximum heart rate by a state of physical rest.

Embodiment 314. The method of any one of embodiments 301-313, wherein the subject's heart rate is elevated to a level that is at least 50% of the subject's maximum heart rate by a state of physical exercise.

Embodiment 315. The method of any one of embodiments 301-313, wherein the subject's heart rate is elevated to a level that is at least 50% of the subject's maximum heart rate by a state of physical exercise, wherein the state of physical exercise is promoted by receiving by the subject an electronic communication medium that provides exercise instruction.

Embodiment 316. The method of any one of embodiments 301-313, wherein the subject's heart rate is elevated to a level that is at least 50% of the subject's maximum heart rate by a state of physical exercise, wherein the state of physical exercise is promoted by receiving by the subject an electronic communication medium that provides exercise instruction, wherein the electronic communication medium is processed by a computer system that is in communication with a biometric device that is in contact with the subject.

Embodiment 317. The method of any one of embodiments 301-313, wherein the subject's heart rate is elevated to a level that is at least 50% of the subject's maximum heart rate by promoting a state of physical exercise for the subject, wherein the state of physical exercise is promoted by receiving by the subject an electronic communication medium that provides exercise instruction, wherein the electronic communication medium is processed by a computer system that is in communication with a biometric device that is in contact with the subject, wherein the computer system: 1) receives a reading of a biometric parameter of the subject at a time point from the biometric device; and 2) communicates the reading of the biometric parameter to the subject.

Embodiment 318. The method of any one of embodiments 301-313, wherein the subject's heart rate is elevated to a level that is at least 50% of the subject's maximum heart rate by a state of physical exercise, wherein the state of physical exercise is promoted by receiving by the subject an electronic communication medium that provides exercise instruction, wherein the electronic communication medium is processed by a computer system that is in communication with a biometric device that is in contact with the subject, wherein the computer system: 1) receives a reading of a biometric parameter of the subject at a time point from the biometric device; and 2) determines based on the biometric parameter the suitability at the time point for the subject of an exercise instruction presented to the subject.

Embodiment 319. The method of any one of embodiments 301-313, wherein the subject's heart rate is elevated to a level that is at least 50% of the subject's maximum heart rate by a state of physical exercise, wherein the state of physical exercise is promoted by receiving by the subject an electronic communication medium that provides exercise instruction, wherein the electronic communication medium is processed by a computer system that is in communication with a biometric device that is in contact with the subject, wherein the computer system: 1) receives a reading of a biometric parameter of the subject at a time point from the biometric device; 2) determines based on the biometric parameter that an exercise instruction presented to the subject is unsuitable for the subject at the time point; 3) alerts the subject that the biometric parameter has deviated from a target range; 4) stops the presentation of the electronic communication medium; and 5) presents to the subject, based on the biometric parameter, an alternative electronic communication medium that provides an alternative exercise instruction that is suitable for the subject.

Embodiment 320. The method of any one of embodiments 301-319, wherein the subject communicates a selection of an exercise to perform to a computer system, wherein the computer system determines a level of the adjusted dose of insulin based on the exercise to perform and a reading of a biometric device that is in contact with the subject.

Embodiment 321. The method of embodiment 320, wherein the subject receives exercise instruction from the computer system based on the exercise to perform and the reading of the biometric device that is in contact with the subject.

Embodiment 322. The method of any one of embodiments 315-321, wherein the electronic communication medium is a video.

Embodiment 323. The method of any one of embodiments 316-322, wherein the biometric device monitors the subject's glucose level.

Embodiment 324. The method of any one of embodiments 316-323, wherein the biometric device monitors the subject's heart rate.

Embodiment 325. The method of any one of embodiments 320-321, wherein the subject receives from the computer system an indication of the suitability of the exercise for the subject based on the reading of the biometric device that is in contact with the subject.

Embodiment 326. The method of any one of embodiments 320-321, wherein the subject receives from the computer system an indication that the exercise is unsuitable for the subject based on the reading of the biometric device that is in contact with the subject.

Embodiment 327. The method of any one of embodiments 320-321, wherein the subject receives from the computer system an instruction to perform an alternative exercise instruction that is suitable for the subject based on the reading of the biometric device that is in contact with the subject.

Embodiment 401. A system comprising: a) a telecommunications device; b) an insulin delivery device that is: 1) in contact with a subject; 2) in communication with the telecommunications device; 3) configured to administer insulin to the subject; and 4) configured to receive from the telecommunications device a transmission of an instruction to administer to the subject a dose of insulin; and c) a glucose monitoring device that is: 1) in contact with the subject; 2) in communication with the telecommunications device; 3) configured to detect a glucose level in the subject; and 4) configured to transmit to the telecommunications device a reading of the glucose level in the subject, wherein the telecommunications device sends a transmission from the telecommunications device to the insulin delivery device, wherein the transmission instructs the insulin delivery device to administer to the subject an adjusted dose of insulin over a period of at least 30 minutes, wherein the adjusted dose of insulin is from about 5% to about 95% of a basal dose of insulin for the subject.

Embodiment 402. The system of embodiment 1, wherein the telecommunications device is configured to display the glucose level detected in the subject by the glucose monitoring device.

Embodiment 403. The system of any one of embodiments 401-402, wherein the insulin delivery device is configured to adjust an amount of insulin that is administered to the subject based on the glucose level detected in the subject by the glucose monitoring device.

Embodiment 404. The system of any one of embodiments 401-403, wherein the insulin delivery device and the glucose monitoring device are in a common housing.

Embodiment 405. The system of any one of embodiments 401-403, wherein the insulin delivery device, the glucose monitoring device, and the telecommunications device are in a common housing.

Embodiment 406. The system of any one of embodiments 401-403, further comprising a glucagon delivery device that is: 1) in contact with the subject; 2) in communication with the telecommunications device; 3) configured to administer glucagon to the subject; and 4) configured to receive from the telecommunications device an instruction to administer to the subject a dose of glucagon.

Embodiment 407. The system of embodiment 406, wherein the insulin delivery device and the glucagon delivery device are in a common housing.

Embodiment 408. The system of embodiment 406, wherein the insulin delivery device, the glucose monitoring device, and the glucagon delivery device are in a common housing.

Embodiment 409. The system of embodiment 406, wherein the insulin delivery device, the glucose monitoring device, the glucagon delivery device, and the telecommunications device are in a common housing.

Embodiment 410. The system of any one of embodiments 406-409, wherein the glucagon delivery device is configured to adjust an amount of glucagon that is administered to the subject based on the glucose level detected in the subject by the glucose monitoring device.

Embodiment 411. The system of any one of embodiments 401-410, wherein the transmission from the telecommunications device to the insulin delivery device instructs the insulin delivery device to administer to the subject an adjusted dose of insulin over a period of at least 60 minutes.

Embodiment 412. The system of any one of embodiments 401-411, wherein the adjusted dose of insulin is about 15% of the basal dose of insulin.

Embodiment 413. The system of any one of embodiments 401-411, wherein the adjusted dose of insulin is about 50% of the basal dose of insulin.

Embodiment 414. The system of any one of embodiments 401-411, wherein the adjusted dose of insulin is about 85% of the basal dose of insulin.

Embodiment 415. The system of any one of embodiments 401-411, wherein the adjusted dose of insulin is about 90% of the basal dose of insulin.

Embodiment 416. The system of any one of embodiments 401-415, wherein the telecommunications device is in communication with a media device, wherein the telecommunications device instructs the media device to present to the subject an instructional exercise electronic communication medium based on the glucose level detected in the subject by the glucose monitoring device.

Embodiment 417. The system of embodiment 416, wherein the electronic communication medium is a video.

Embodiment 418. The system of any one of embodiments 401-417, wherein the telecommunications device is configured to determine a level of the dose of insulin based on an input of an exercise to be performed by the subject and the reading of the glucose level in the subject by the glucose monitoring device.

Embodiment 419. The system of any one of embodiments 401-418, wherein any device or housing is implanted in the subject.

Embodiment 501. A system comprising: a) a telecommunications device; b) an insulin delivery device that is: 1) in contact with a subject; 2) in communication with the telecommunications device; 3) configured to administer insulin to the subject; and 4) configured to receive from the telecommunications device a transmission of an instruction to administer to the subject a dose of insulin; c) a glucose monitoring device that is: 1) in contact with the subject; 2) in communication with the telecommunications device; 3) configured to detect a glucose level in the subject; and 4) configured to transmit to the telecommunications device a reading of the glucose level in the subject; and d) a heart rate monitor device that is: 1) in contact with the subject; 2) in communication with the telecommunications device; 3) configured to detect a heart rate in the subject; and 4) configured to transmit to the telecommunications device a reading of the heart rate in the subject, wherein the telecommunications device sends a transmission from the telecommunications device to the insulin delivery device, wherein the transmission instructs the insulin delivery device, based on the reading of the heart rate of the subject, to administer to the subject an adjusted dose of insulin over a period of at least 30 minutes, wherein the adjusted dose of insulin is from about 5% to about 95% of a basal dose of insulin for the subject.

Embodiment 502. The system of embodiment 501, wherein the telecommunications device is configured to display the glucose level detected in the subject by the glucose monitoring device and the heart rate detected in the subject by the heart rate monitoring device.

Embodiment 503. The system of any one of embodiments 501-502, wherein the insulin delivery device is configured to adjust an amount of insulin that is administered to the subject based on the glucose level detected in the subject by the glucose monitoring device and the heart rate detected in the subject by the heart rate monitoring device.

Embodiment 504. The system of any one of embodiments 501-503, wherein the insulin delivery device and the glucose monitoring device are in a common housing.

Embodiment 505. The system of any one of embodiments 501-503, wherein the insulin delivery device, the glucose monitoring device, and the heart rate monitoring device are in a common housing.

Embodiment 506. The system of any one of embodiments 501-503, wherein the insulin delivery device, the glucose monitoring device, and the telecommunications device are in a common housing.

Embodiment 507. The system of any one of embodiments 501-503, wherein the insulin delivery device, the glucose monitoring device, the heart rate monitoring device, and the telecommunications device are in a common housing Embodiment 508. The system of any one of embodiments 501-507, further comprising a glucagon delivery device that is: 1) in contact with a subject; 2) in communication with the telecommunications device; 3) configured to administer glucagon to the subject; and 4) configured to receive from the telecommunications device an instruction to administer to the subject a dose of glucagon.

Embodiment 509. The system of embodiment 508, wherein the insulin delivery device and the glucagon delivery device are in a common housing.

Embodiment 510. The system of embodiment 508, wherein the insulin delivery device, the glucose monitoring device, the heart rate monitoring device, and the glucagon delivery device are in a common housing.

Embodiment 511. The system of embodiment 508, wherein the insulin delivery device, the glucose monitoring device, the heart rate monitoring device, the glucagon delivery device, and the telecommunications device are in a common housing.

Embodiment 512. The system of embodiment 508, wherein the glucagon delivery device is configured to adjust an amount of glucagon that is administered to the subject based on the glucose level detected in the subject by the glucose monitoring device and the heart rate detected in the subject by the heart rate monitoring device.

Embodiment 513. The system of any one of embodiments 501-512, wherein the transmission from the telecommunications device to the insulin delivery device instructs the insulin delivery device to administer to the subject an adjusted dose of insulin over a period of at least 60 minutes.

Embodiment 514. The system of any one of embodiments 501-513, wherein the adjusted dose of insulin is about 15% of the basal dose of insulin.

Embodiment 515. The system of any one of embodiments 501-513, wherein the adjusted dose of insulin is about 50% of the basal dose of insulin.

Embodiment 516. The system of any one of embodiments 501-513, wherein the adjusted dose of insulin is about 85% of the basal dose of insulin.

Embodiment 517. The system of any one of embodiments 501-513, wherein the adjusted dose of insulin is about 90% of the basal dose of insulin.

Embodiment 518. The system of any one of embodiments 501-517, wherein the telecommunications device is in communication with a media device, wherein the telecommunications device instructs the media device to present to the subject an instructional exercise electronic communication medium based on the glucose level detected in the subject by the glucose monitoring device and the heart rate detected in the subject by the heart rate monitoring device.

Embodiment 519. The system of embodiment 518, wherein the electronic communication medium is a video.

Embodiment 520. The system of any one of embodiments 501-519, wherein the telecommunications device is configured to determine a level of the dose of insulin based on an input of an exercise to be performed by the subject, the reading of the glucose level in the subject by the glucose monitoring device, and the heart rate detected in the subject by the heart rate monitoring device.

Embodiment 521. The system of any one of embodiments 501-520, wherein any device or housing is implanted in the subject.

Embodiment 601. A system comprising: a) an insulin delivery device that is: 1) in contact with a subject; 2) configured to administer insulin to the subject; and 3) configured to receive a transmission of an instruction to administer to the subject a dose of insulin; and b) a glucose monitoring device that is: 1) in contact with the subject; 2) in communication with the insulin delivery device; 3) configured to detect a glucose level in the subject; and 4)

configured to transmit to the insulin delivery device an instruction to administer to the subject the dose of insulin based on the detected glucose level in the subject, wherein the insulin delivery device comprises a processor and a computer-readable medium with a computer-executable code encoded thereon, wherein the computer-executable code instructs the insulin delivery device to administer to the subject an adjusted dose of insulin over a period of at least 30 minutes, wherein the adjusted dose of insulin is from about 5% to about 95% of a basal dose of insulin for the subject, and wherein the processor processes the computer-executable code.

Embodiment 602. The system of embodiment 601, wherein the insulin delivery device is configured to adjust an amount of insulin that is administered to the subject based on the glucose level detected in the subject by the glucose monitoring device.

Embodiment 603. The system of any one of embodiments 601-602, further comprising a glucagon delivery device that is: 1) in contact with the subject; 2) in communication with the insulin delivery device; 3) configured to administer glucagon to the subject; and 4) configured to receive from the insulin delivery device an instruction to administer to the subject a dose of glucagon.

Embodiment 604. The system of embodiment 603, wherein the insulin delivery device and the glucagon delivery device are in a common housing.

Embodiment 605. The system of any one of embodiments 603-604, wherein the glucagon delivery device is configured to adjust an amount of glucagon that is administered to the subject based on the glucose level detected in the subject by the glucose monitoring device.

Embodiment 606. The system of any one of embodiments 601-605, wherein the transmission instructs the insulin delivery device to administer to the subject an adjusted dose of insulin over a period of at least 60 minutes.

Embodiment 607. The system of any one of embodiments 601-606, wherein the adjusted dose of insulin is about 15% of the basal dose of insulin.

Embodiment 608. The system of any one of embodiments 601-606, wherein the adjusted dose of insulin is about 50% of the basal dose of insulin.

Embodiment 609. The system of any one of embodiments 601-606, wherein the adjusted dose of insulin is about 85% of the basal dose of insulin.

Embodiment 610. The system of any one of embodiments 601-606, wherein the adjusted dose of insulin is about 90% of the basal dose of insulin.

Embodiment 611. The system of any one of embodiments 601-610, further comprising a telecommunications device that is: 1) in communication with the insulin delivery device; 2) in communication with the glucose monitoring device; 3) configured to transmit to the insulin delivery device an instruction to administer to the subject the dose of insulin; and 4) configured to receive from the glucose monitoring device a transmission of a reading of the glucose level in the subject, wherein the insulin delivery device is configured to receive from the telecommunications device an instruction to administer to the subject the dose of insulin; and the glucose monitoring device is configured to transmit to the telecommunications device the reading of the glucose level in the subject.

Embodiment 612. The system of embodiment 611, wherein the telecommunications device is configured to display the glucose level detected in the subject by the glucose monitoring device.

Embodiment 613. The system of any one of embodiments 611-612, wherein the telecommunications device is in communication with a media device, wherein the telecommunications device instructs the media device to present to the subject an instructional exercise electronic communication medium based on the glucose level detected in the subject by the glucose monitoring device.

Embodiment 614. The system of embodiment 613, wherein the electronic communication medium is a video.

Embodiment 615. The system of any one of embodiments 601-614, wherein any device or housing is implanted in the subject.

Embodiment 701. A system comprising: a) an insulin delivery device that is: 1) in contact with a subject; 2) configured to administer insulin to the subject; and 3) configured to receive a transmission of an instruction to administer to the subject a dose of insulin; and b) a glucose monitoring device that is: 1) in contact with the subject; 2) in communication with the insulin delivery device; 3) configured to detect a glucose level in the subject; and 4) configured to transmit to the insulin delivery device an instruction to administer to the subject the dose of insulin based on the detected glucose level in the subject, wherein the glucose monitoring device sends a transmission from the glucose monitoring device to the insulin delivery device, wherein the transmission instructs the insulin delivery device to administer to the subject an adjusted dose of insulin over a period of at least 30 minutes, wherein the adjusted dose of insulin is from about 5% to about 95% of a basal dose of insulin for the subject.

Embodiment 702. The system of embodiment 701, wherein the insulin delivery device is configured to adjust an amount of insulin that is administered to the subject based on the glucose level detected in the subject by the glucose monitoring device.

Embodiment 703. The system of any one of embodiments 701-702, further comprising a glucagon delivery device that is: 1) in contact with the subject; 2) in communication with the glucose monitoring device; 3) configured to administer glucagon to the subject; and 4) configured to receive from the glucose monitoring device an instruction to administer to the subject a dose of glucagon.

Embodiment 704. The system of embodiment 703, wherein the insulin delivery device and the glucagon delivery device are in a common housing.

Embodiment 705. The system of any one of embodiments 703-704, wherein the glucagon delivery device is configured to adjust an amount of glucagon that is administered to the subject based on the glucose level detected in the subject by the glucose monitoring device.

Embodiment 706. The system of any one of embodiments 701-705, wherein the transmission instructs the insulin delivery device to administer to the subject an adjusted dose of insulin over a period of at least 60 minutes.

Embodiment 707. The system of any one of embodiments 701-706, wherein the adjusted dose of insulin is about 15% of the basal dose of insulin.

Embodiment 708. The system of any one of embodiments 701-706, wherein the adjusted dose of insulin is about 50% of the basal dose of insulin.

Embodiment 709. The system of any one of embodiments 701-706, wherein the adjusted dose of insulin is about 85% of the basal dose of insulin.

Embodiment 710. The system of any one of embodiments 701-706, wherein the adjusted dose of insulin is about 90% of the basal dose of insulin.

Embodiment 711. The system of any one of embodiments 701-710, further comprising a telecommunications device that is: 1) in communication with the insulin delivery device; 2) in communication with the glucose monitoring device; 3) configured to transmit to the insulin delivery device an instruction to administer to the subject the dose of insulin; and 4) configured to receive from the glucose monitoring device a transmission of a reading of the glucose level in the subject, wherein the insulin delivery device is configured to receive from the telecommunications device an instruction to administer to the subject the dose of insulin; and the glucose monitoring device is configured to transmit to the telecommunications device the reading of the glucose level in the subject.

Embodiment 712. The system of embodiment 711, wherein the telecommunications device is configured to display the glucose level detected in the subject by the glucose monitoring device.

Embodiment 713. The system of any one of embodiments 711-712, wherein the telecommunications device is in communication with a media device, wherein the telecommunications device instructs the media device to present to the subject an instructional exercise electronic communication medium based on the glucose level detected in the subject by the glucose monitoring device.

Embodiment 714. The system of embodiment 713, wherein the electronic communication medium is a video.

Embodiment 715. The system of any one of embodiments 701-714, wherein any device or housing is implanted in the subject.

Embodiment 801. A kit comprising: a) an insulin delivery device; and b) a glucose monitoring device, wherein the insulin delivery device comprises a processor and a computer-readable medium with a computer-executable code encoded thereon, wherein the computer-executable code instructs the insulin delivery device to administer to a subject an adjusted dose of insulin over a period of at least 30 minutes, wherein the adjusted dose of insulin is from about 5% to about 95% of a basal dose of insulin for the subject, and wherein the processor processes the computer-executable code.

Embodiment 802. The kit of embodiment 801, further comprising a glucagon delivery device.

Embodiment 803. The kit of embodiment 802, wherein the insulin delivery device and the glucagon delivery device are in a common housing.

Embodiment 804. The kit of any one of embodiments 801-803, wherein the computer-executable code instructs the insulin delivery device to administer to a subject the adjusted dose of insulin over a period of at least 60 minutes.

Embodiment 805. The kit of any one of embodiments 801-804, wherein the adjusted dose of insulin is about 15% of the basal dose of insulin.

Embodiment 806. The kit of any one of embodiments 801-804, wherein the adjusted dose of insulin is about 50% of the basal dose of insulin.

Embodiment 807. The kit of any one of embodiments 801-804, wherein the adjusted dose of insulin is about 85% of the basal dose of insulin.

Embodiment 808. The kit of any one of embodiments 801-804, wherein the adjusted dose of insulin is about 90% of the basal dose of insulin.

Embodiment 809. The kit of any one of embodiments 801-804, further comprising a telecommunications device.

Embodiment 810. The kit of embodiment 1, further comprising a heart rate monitor device.

Embodiment 901. A kit comprising: a) a telecommunications device; b) an insulin delivery device; and c) a glucose monitoring device, wherein the telecommunications device comprises a processor and a computer-readable medium with a computer-executable code encoded thereon, wherein the computer-executable code instructs the telecommunications device to transmit to the insulin delivery device an instruction to administer to a subject an adjusted dose of insulin over a period of at least 30 minutes, wherein the adjusted dose of insulin is from about 5% to about 95% of a basal dose of insulin for the subject, and wherein the processor processes the computer-executable code.

Embodiment 902. The kit of embodiment 901, further comprising a glucagon delivery device.

Embodiment 903. The kit of embodiment 902, wherein the insulin delivery device and the glucagon delivery device are in a common housing.

Embodiment 904. The kit of any one of embodiments 901-903, wherein the computer-executable code instructs the insulin delivery device to administer to a subject the adjusted dose of insulin over a period of at least 60 minutes.

Embodiment 905. The kit of any one of embodiments 901-904, wherein the adjusted dose of insulin is about 15% of the basal dose of insulin.

Embodiment 906. The kit of any one of embodiments 901-904, wherein the adjusted dose of insulin is about 50% of the basal dose of insulin.

Embodiment 907. The kit of any one of embodiments 901-904, wherein the adjusted dose of insulin is about 85% of the basal dose of insulin.

Embodiment 908. The kit of any one of embodiments 901-904, wherein the adjusted dose of insulin is about 90% of the basal dose of insulin.

Embodiment 909. The kit of any one of embodiments 901-908, further comprising a heart rate monitor device.

Embodiment 1001. A kit comprising: a) an insulin delivery device; and b) a glucose monitoring device, wherein the glucose monitoring device comprises a processor and a computer-readable medium with a computer-executable code encoded thereon, wherein the computer-executable code instructs the glucose monitoring device to transmit to the insulin delivery device an instruction to administer to a subject an adjusted dose of insulin over a period of at least 30 minutes, wherein the adjusted dose of insulin is from about 5% to about 95% of a basal dose of insulin for the subject, and wherein the processor processes the computer-executable code.

Embodiment 1002. The kit of embodiment 1001, further comprising a glucagon delivery device.

Embodiment 1003. The kit of embodiment 1002, wherein the insulin delivery device and the glucagon delivery device are in a common housing.

Embodiment 1004. The kit of any one of embodiments 1001-1003, wherein the computer-executable code instructs the insulin delivery device to administer to a subject the adjusted dose of insulin over a period of at least 60 minutes.

Embodiment 1005. The kit of any one of embodiments 1001-1004, wherein the adjusted dose of insulin is about 15% of the basal dose of insulin.

Embodiment 1006. The kit of any one of embodiments 1001-1004, wherein the adjusted dose of insulin is about 50% of the basal dose of insulin.

Embodiment 1007. The kit of any one of embodiments 1001-1004, wherein the adjusted dose of insulin is about 85% of the basal dose of insulin.

Embodiment 1008. The kit of any one of embodiments 1001-1004, wherein the adjusted dose of insulin is about 90% of the basal dose of insulin.

Embodiment 1009. The kit of any one of embodiments 1001-1008, further comprising a telecommunications device.

Embodiment 1010. The kit of any one of embodiments 1001-1009, further comprising a heart rate monitor device.

Embodiment 1101. A method comprising: a) presenting by a media device to a subject an electronic communication medium that provides instruction for physical exercise, wherein the subject is diabetic, wherein the media device is in communication with a receiver; b) monitoring, contemporaneously with presenting to the subject the electronic communication medium that provides instruction for physical exercise, via a glucose monitoring device the subject during a state of physical exercise, wherein the glucose monitoring device detects a blood glucose level in the subject; c) transmitting by a biometric device the blood glucose level of the subject to the receiver; d) receiving by the receiver the blood glucose level of the subject; and e) presenting by the media device an indication of a change in the blood glucose level of the subject in real time contemporaneously with presenting the electronic communication medium that provides instruction for physical exercise.

Embodiment 1102. The method of embodiment 1101, wherein the subject has type 1 diabetes.

Embodiment 1103. The method of embodiment 1101, wherein the subject has type 2 diabetes.

Embodiment 1104. The method of any one of embodiments 1101-1103, wherein the electronic communication medium is a video.

Embodiment 1105. The method of any one of embodiments 1101-1104, further comprising presenting to the subject by the electronic communication medium a warning that a biometric parameter of the subject has reached a value associated with a state of high risk.

Embodiment 1106. The method of any one of embodiments 1101-1105, wherein the receiver is in communication with a processor, wherein the processor determines based on the blood glucose level of the subject the suitability for the subject of an exercise instruction presented to the subject.

Embodiment 1107. The method of any one of embodiments 1101-1105, wherein the receiver is in communication with a processor, wherein the processor determines based on the blood glucose level of the subject that an exercise instruction being presented to the subject is unsuitable for the subject, and instructs the media device to display to the subject an alternative electronic communication medium that provides an alternative exercise instruction that is suitable for the subject based on the blood glucose level of the subject.

Embodiment 1108. The method of any one of embodiments 1101-1107, further comprising monitoring the subject's heart rate by a heart rate monitor, and presenting by the media device an indication of the subject's heart rate contemporaneously with presenting the electronic communication medium that provides instruction for physical exercise.

Embodiment 1109. The method of embodiment 1108, wherein the receiver is in communication with a processor, wherein the processor determines based on the subject's heart rate the suitability for the subject of an exercise instruction presented to the subject.

Embodiment 1110. The method of embodiment 1108, wherein the receiver is in communication with a processor, wherein the processor determines based on the subject's heart rate that an exercise instruction being presented to the subject is unsuitable for the subject, and instructs the media device to display to the subject an alternative electronic communication medium that provides an alternative exercise instruction that is suitable for the subject based on the subject's heart rate.

Embodiment 1111. The method of any one of embodiments 1101-1110, further comprising administering to the subject a dose of insulin based on the blood glucose level of the subject.

Embodiment 1112. The method of any one of embodiments 1101-1111, further comprising administering to the subject a dose of glucose based on the blood glucose level of the subject.

Embodiment 1113. The method of any one of embodiments 1101-1112, further comprising administering to the subject a dose of glucagon based on the blood glucose level of the subject.

Embodiment 1114. The method of any one of embodiments 1101-1113, further comprising receiving by the media device an input of a selection by the subject of an exercise to perform, wherein the presenting by the media device to the subject the electronic communication medium that provides the instruction for the physical exercise is based on the input of the selection by the subject.

What is claimed is:

1. A system comprising:
   a) a telecommunications device;
   b) an insulin delivery device that is:
      1) in contact with a subject;
      2) in communication with the telecommunications device;
      3) configured to administer insulin to the subject; and
      4) configured to receive from the telecommunications device a transmission of an instruction to administer to the subject a dose of insulin;
   c) a glucose monitoring device that is:
      1) in contact with the subject;
      2) in communication with the telecommunications device;
      3) configured to detect a glucose level in the subject; and
      4) configured to transmit to the telecommunications device a reading of the glucose level in the subject; and
   d) a heart rate monitor device that is:
      1) in contact with the subject;
      2) in communication with the telecommunications device;
      3) configured to detect a heart rate in the subject; and
      4) configured to transmit to the telecommunications device a reading of the heart rate in the subject, wherein the telecommunications device sends the transmission from the telecommunications device to the insulin delivery device, wherein the transmission instructs the insulin delivery device, based on the reading of the heart rate of the subject, to administer to the subject during exercise an adjusted dose of insulin over a period of at least 30 minutes, wherein the adjusted dose of insulin is from about 5% to about 95% of a basal dose of insulin for the subject, wherein the telecommunications device is in communication with a media device, wherein the telecommunications device instructs the media device to present to the subject an instructional exercise electronic communication medium based on the glucose level detected in the subject by the glucose monitoring device and the heart rate detected in the subject by the heart rate monitoring device.

2. The system of claim 1, wherein the telecommunications device is configured to display the glucose level detected in the subject by the glucose monitoring device and the heart rate detected in the subject by the heart rate monitoring device.

3. The system of claim 1, wherein the insulin delivery device is configured to adjust an amount of insulin that is administered to the subject based on the glucose level detected in the subject by the glucose monitoring device and the heart rate detected in the subject by the heart rate monitoring device.

4. The system of claim 1, wherein the insulin delivery device and the glucose monitoring device are in a common housing.

5. The system of claim 1, wherein the insulin delivery device, the glucose monitoring device, and the heart rate monitoring device are in a common housing.

6. The system of claim 1, wherein the insulin delivery device, the glucose monitoring device, and the telecommunications device are in a common housing.

7. The system of claim 1, wherein the insulin delivery device, the glucose monitoring device, the heart rate monitoring device, and the telecommunications device are in a common housing.

8. The system of claim 1, further comprising a glucagon delivery device that is:
   1) in contact with the subject;
   2) in communication with the telecommunications device;
   3) configured to administer glucagon to the subject; and
   4) configured to receive from the telecommunications device an instruction to administer to the subject a dose of glucagon.

9. The system of claim 8, wherein the insulin delivery device and the glucagon delivery device are in a common housing.

10. The system of claim 8, wherein the insulin delivery device, the glucose monitoring device, the heart rate monitoring device, and the glucagon delivery device are in a common housing.

11. The system of claim 8, wherein the insulin delivery device, the glucose monitoring device, the heart rate monitoring device, the glucagon delivery device, and the telecommunications device are in a common housing.

12. The system of claim 8, wherein the glucagon delivery device is configured to adjust an amount of glucagon that is administered to the subject based on the glucose level detected in the subject by the glucose monitoring device and the heart rate detected in the subject by the heart rate monitoring device.

13. The system of claim 1, wherein the transmission from the telecommunications device to the insulin delivery device instructs the insulin delivery device to administer to the subject the adjusted dose of insulin over a period of at least 60 minutes.

14. The system of claim 1, wherein the adjusted dose of insulin is about 15% of the basal dose of insulin.

15. The system of claim 1, wherein the adjusted dose of insulin is about 50% of the basal dose of insulin.

16. The system of claim 1, wherein the adjusted dose of insulin is about 85% of the basal dose of insulin.

17. The system of claim 1, wherein the adjusted dose of insulin is about 90% of the basal dose of insulin.

18. The system of claim 1, wherein the instructional exercise electronic communication medium is a video.

19. The system of claim 1, wherein the telecommunications device is configured to determine a level of the dose of insulin based on an input of an exercise to be performed by the subject, the reading of the glucose level in the subject by the glucose monitoring device, and the reading of the heart rate in the subject by the heart rate monitoring device.

20. The system of claim 1, wherein the instructional exercise electronic communication medium is selected to achieve a diabetes metric, wherein the diabetes metric is A1C reduction, increased fat metabolism, increased weight loss, real-time decrease of blood glucose levels, increase in insulin sensitivity, or decrease in insulin resistance.

* * * * *

UNITED STATES PATENT AND TRADEMARK OFFICE
CERTIFICATE OF CORRECTION

| | | |
|---|---|---|
| PATENT NO. | : 9,861,310 B2 | Page 1 of 1 |
| APPLICATION NO. | : 14/885825 | |
| DATED | : January 9, 2018 | |
| INVENTOR(S) | : Charles O'Connell | |

It is certified that error appears in the above-identified patent and that said Letters Patent is hereby corrected as shown below:

On the Title Page

In item (71):
Please replace -Exerscrip, LLC, New Haven, CT (US)- with --Fitscript, LLC, New Haven, CT (US)--.

Signed and Sealed this
Tenth Day of July, 2018

Andrei Iancu
*Director of the United States Patent and Trademark Office*